US006872827B2

(12) United States Patent
Webb et al.

(10) Patent No.: US 6,872,827 B2
(45) Date of Patent: Mar. 29, 2005

(54) SOMATOSTATIN ANALOGUE COMPOUNDS

(75) Inventors: Thomas Webb, Encinitas, CA (US); Donatella Chianelli, San Diego, CA (US); Yong-Chul Kim, Gwangju (KR)

(73) Assignee: Chembridge Research Laboratories, Inc., San Diego, CA (US)

( * ) Notice: Subject to any disclaimer, the term of this patent is extended or adjusted under 35 U.S.C. 154(b) by 0 days.

(21) Appl. No.: 10/350,158

(22) Filed: Jan. 23, 2003

(65) Prior Publication Data
US 2004/0019069 A1 Jan. 29, 2004

Related U.S. Application Data
(60) Provisional application No. 60/375,635, filed on Apr. 26, 2002.

(51) Int. Cl.[7] ............................................. C07D 221/20
(52) U.S. Cl. ..................................... 546/16; 546/278
(58) Field of Search ............................. 546/16; 514/278

(56) References Cited

U.S. PATENT DOCUMENTS

| | | | |
|---|---|---|---|
| 4,016,100 A | 4/1977 | Suzuki et al. | 252/316 |
| 4,348,384 A | 9/1982 | Horikoshi et al. | 424/101 |
| 4,659,774 A | 4/1987 | Webb et al. | 525/54.2 |
| 5,120,859 A | 6/1992 | Webb | 548/557 |
| 5,283,293 A | 2/1994 | Webb | 525/332.2 |
| 5,367,072 A | 11/1994 | Webb | 540/483 |
| 5,371,072 A | 12/1994 | Webb et al. | 514/18 |
| 5,492,895 A | 2/1996 | Vlasuk et al. | 514/18 |
| 5,514,777 A | 5/1996 | Webb et al. | 530/331 |
| 5,534,498 A | 7/1996 | Brunck et al. | 514/19 |
| 5,597,804 A | 1/1997 | Webb et al. | 514/18 |
| 5,656,600 A | 8/1997 | Abelman et al. | 514/13 |
| 5,670,479 A | 9/1997 | Abelman et al. | 514/12 |
| 5,714,580 A | 2/1998 | Brunck et al. | 530/331 |
| 5,731,413 A | 3/1998 | Webb et al. | 530/331 |
| 5,739,112 A | 4/1998 | Brunck et al. | 514/19 |
| 5,795,905 A | 8/1998 | McCarthy et al. | 514/383 |
| 5,869,454 A | 2/1999 | Webb et al. | 514/18 |
| 5,883,077 A | 3/1999 | Brunck et al. | 514/19 |
| 5,886,146 A | 3/1999 | Vlasuk et al. | 530/331 |
| 5,955,576 A | 9/1999 | Vlasuk et al. | 530/331 |
| 6,025,372 A | 2/2000 | Yang et al. | 514/316 |
| 6,211,195 B1 | 4/2001 | Webb et al. | 514/301 |
| 6,255,310 B1 | 7/2001 | Webb et al. | 514/258 |
| 6,288,060 B1 | 9/2001 | Webb et al. | 514/235.8 |
| 6,316,437 B1 | 11/2001 | Hoffman et al. | 514/212.02 |
| 6,469,166 B2 | 10/2002 | Webb et al. | 544/278 |

FOREIGN PATENT DOCUMENTS

| | | |
|---|---|---|
| EP | 0365556 | 5/1990 |
| EP | 0627929 | 12/1994 |
| EP | 0664786 | 8/1995 |
| EP | 0675899 | 10/1995 |
| EP | 0684830 | 12/1995 |
| EP | 0790982 | 8/1997 |
| EP | 0863882 | 9/1998 |
| EP | 0882051 | 12/1998 |
| GB | 2355264 | 4/2001 |
| JP | 2002121194 | 4/2002 |
| WO | 8809796 | 12/1988 |
| WO | 9104247 | 4/1991 |
| WO | 9312076 | 6/1993 |
| WO | 9314779 | 8/1993 |
| WO | 9315756 | 8/1993 |
| WO | 9408941 | 4/1994 |
| WO | 9413693 | 6/1994 |
| WO | 9417817 | 8/1994 |
| WO | 9421673 | 9/1994 |
| WO | 9535280 | 12/1995 |
| WO | 9639400 | 12/1996 |
| WO | 9510527 | 4/1997 |
| WO | 9714684 | 4/1997 |
| WO | 9729109 | 8/1997 |
| WO | 9729110 | 8/1997 |
| WO | 9847903 | 10/1998 |
| WO | 9941216 | 8/1999 |
| WO | 0158878 | 8/2001 |
| WO | 0158879 | 8/2001 |
| WO | 03090677 | 11/2003 |
| WO | 2003090677 | * 11/2003 |

OTHER PUBLICATIONS

Brazeau et al., "Hypothalamic Polypeptide That Inhibits the Secretation of Immunoreactive Pituitary Growth Hormone," *Science* 179:77–79 (1972).

(Continued)

Primary Examiner—Rita Desai
(74) Attorney, Agent, or Firm—Fish & Richardson P.C.

(57) ABSTRACT

Compounds having somatostatin activity of the following Formula I,

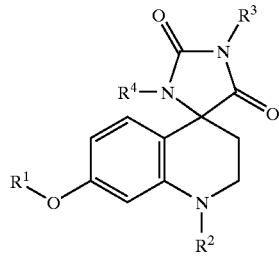

Formula I wherein, $R^1$ is aryl, substituted-aryl, and aryl-(lower-alkyl)-;

$R^2$ is lower alkyl, amino substituted lower alkyl, -carboxy-(lower-alkyl), -carbamic acid-(lower-alkyl) and -carboxy-(lower-alkyl)-aryl; and $R^3$ and $R^4$ are independently, lower-alkyl, aryl, substituted-aryl, (substituted-aryl)-(lower-alkyl)-, heteroaryl, (heteroaryl)-(lower-alkyl)-, substituted-heteroaryl, (substituted heteroaryl)-(lower-alkyl)-, heterocyclic, heterocyclic-(lower-alkyl)-, substituted-heterocyclic, (substituted-heterocyclic)-(lower alkyl)-, -carboxy-(lower-alkyl), and -carboxy-(lower-alkyl)-aryl; or a pharmaceutically acceptable, ester, ether, or salt thereof; methods for their use; and preparation.

9 Claims, No Drawings

OTHER PUBLICATIONS

Chen et al., "Design and Synthesis of a Series of Non–Peptide High–Affinity Human Corticotropin–Releasing Factor$_1$ Receptor Antagonists," *J. Med. Chem.* 39(22):4358–4360 (1996).

Cheng and Prusoff, "Relationship Between the Inhibition Constant ($K_1$) and the Concentration of Inhibitor Which Causes 50 Per Cent Inhibition ($I_{50}$) of an Enzymatic Reaction," *Biochem. Pharmacol.* 22:3099–3108 (1973).

Eppstein et al., Controlled–Release and Localized Targeting of Interferons, in *Delivery Systems for Peptide Drugs* Davis et al. (Eds.) New York: Tomlinson, Plenum Pub. Corp. pp. 277–283 (1986).

Eppstein et al., "Liposome–Encapsulated Muramyl Dipeptide Analogue" *Int. J. Immunotherapy* 11(2):115–126 (1986).

Feniuk, W. et al., "Characterization of somatostatin receptors in guinea–pig isolated ileum, vas deferens and right atrium," *Br. J. Pharmacol.* 110:1156–1164 (1993).

Gabizon et al., Liposomes as in Vivo Carriers of Adriamycin: Reduced Cardiac Uptake and Preserved Antitumor Activity in Mice, *Cancer Res.* 42:4734–4739 (1982).

Garland S. L. and Dean P. M., "Design criteria for molecular mimics of fragments of the β–turn. 1. Cα atom analysis," *J. Comp. Aided Mole. Des.* 13:469–483 (1999).

Gotfredsen et al., "Cellular Localization of Stable Solid Liposomes in the Liver of Rats," *Biochemical Pharmacology* 32(22):3389–3396 (1983).

Hirschmann, R., "De Novo Design and Synthesis of Somatostatin Non–Peptide Peptidomimetics Utilizing β–D–Glucose as a Novel Scaffolding," *J. Am. Chem. Soc.* 115(26):12550–12568 (1993).

Huang et al., "Synthesis and SAR of 8–Arylquinolines as Potent Coirticotropin–Releasing Factor$_1$ (CRF$_1$) Receptor Antagonists," *Bioorg Med Chem Lett.* 13(19):3375–3379 (2003).

Hunt, C.A., "Liposomes Disposition in Vivo: V. Liposome Stability in Plasma and Implications for Drug Carrier Function," *Biochemica et Biophysica Acta.* 719:450–463 (1982).

Liapakis et al., "Identification of Ligand Binding Determinants in the Somatostatin Receptor Subtypes 1 and 2," *J. Biol. Chem.* 271(34):20331–20339 (1996).

Lopez–Berestein et al., "Liposomal Amphotericin B for the Treatment of Systemic Fungal Infections in Patients with Cancer: A Preliminary Study," *J. Infect. Dis.* 151(4):704–710 (1985).

Olson et al., "Characterization, Toxicity and Therapeutic Efficacy of Adriamycin Encapsulated in Liposomes," *Eur. J. Cancer Clin. Oncol.* 18:167–176 (1982).

Patel, Y.C. and Srikant, C.B., "Subtype Selectivity of Peptide Analogs for All Five Cloned Human Somatostatin Receptors (hsstr 1–5)," *Endocrinology* 135(6):2814–2817 (1994).

Reisine, T. and Bell, G.I., "Molecular Biology of Somatostatin Receptors," *Endocrine Reviews* 16(4):427–442 (1995).

Senior et al., "Tissue distribution of liposomes exhibiting long half–lives in the circulation after intravenous injection," *Biochemica et Biophysica Acta.* 839:1–8 (1985).

Webb et al., "Epidural haematoma presenting as polymorphic ventricular tachycardia," *Heart.* 89(3):316 (2003).

Webb et al. "Quinazolines as Adenosine Receptor Antagonists: SAR and Selectivity for $A_{2B}$ Receptors," *Bioorg Med Chem.* 11(1):77–85 (2003).

Webb et al. "The Utilization of a Unified Pharmacophore Query in the Discovery of New Antagonists of the Adenosine Receptor Family," *Bioorg Med Chem Lett.* 10(1):31–34 (2000).

Weinstein et al., "Liposomes as Drug Carriers in Cancer Chemotherapy," *Pharmac. Ther.* 24:207–233 (1983).

Whitten et al., "Rapid Microscale Synthesis, a New Method for Lead Optimization Using Robotics and Solution Phase Chemistry: Application to the Synthesis and Optimization of Corticotropin–Releasing Factor$_1$ Receptor Antagonists," *J. Med. Chem.* 39(22):4354–4357 (1996).

* cited by examiner

SOMATOSTATIN ANALOGUE COMPOUNDS

This application claims the benefit of U.S. Provisional Application No. 60/375,635, filed Apr. 26, 2002, incorporated herein by reference.

BACKGROUND OF THE INVENTION

1. Field of the Invention

The invention relates generally to pharmaceuticals, and more specifically to somatostatin analogue compounds, their use and preparation.

2. Background Information

Somatostatin (somatotrophin release-inhibiting factor) was first isolated and characterized by Brazeau et al. (Brazeau, P., Vale, W., Burgus, R., Ling, N., Butcher, M., Rivier, J., and Guillemin, R., Science, 1972, 179, 77–79). Somatostatin (SRIF) is a cyclic peptide that is widely distributed throughout the body. SRIF occurs in two major forms, 14- and 28-amino acid forms. There have been five SRIF receptors identified and cloned from human tissue (sst-1 to sst-5). All five receptors are members of the G protein-linked receptor family.

SRIF is widely distributed throughout the body. It has important regulatory effects on a variety of endocrine and exocrine functions in the body. SRIF inhibits the release of several hormones, including growth hormone from the anterior pituitary, insulin and glucagon from the pancreas, gastrin from the gastrointestinal tract. It also has antiproliferative activity, and acts as a neurotransmitter, or neuromodulator in the brain. As such, SRIF has been recognized as an important nexus of a number of physiological functions that are in turn involved in various disease states. It has also been recognized that such diseases can be treated through the use of compounds/drugs that have enhanced SRIF activity, such as increased potency, or longer half-life.

An example of such a compound is Sandostatin (octreotide acetate). Sandostatin is a cyclic 8-amino acid peptide analogue of somatostatin. A long-acting release formulation of Sandostatin, known commercially as, Sandostatin Lar Deport, was approved by the United States Food and Drug Administration in 1998 for the treatment of acromegaly, and to control severe diarrhea and flushing associated with metastatic carcinoid tumors, and vasoactive intestinal peptide secreting tumors (VIPomas).

Sandostatin Lar Depot mechanism of action is mimicking SRIF. Sandostatin Lar Depot has been found to reduce and normalize levels of IGF-1 (insulin growth factor) and growth hormone. Although Sandostatin is a commercially viable and useful compound, it has the inherent disadvantage of having a peptide structure. It is recognized by those of ordinary skill in the art that the peptide compounds are generally more costly to manufacture than organic molecules, and often have undesirable pharmacologic characteristics, such as short half-life, and low solubility.

Accordingly, there are unmet needs for non-peptidic SRIF analogues that can be used for the treatment of disease states that are effected by SRIF. The present invention fulfills these needs and further provides other related advantages.

SUMMARY OF THE INVENTION

The present invention provides a compound of Formula I, as follows,

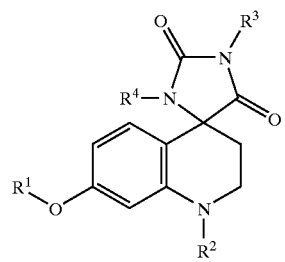

Formula I wherein, $R^1$ is hydrogen, lower-alkyl, substituted lower-alkyl, aryl, substituted-aryl, aryl-(lower-alkyl)-, (substituted-aryl)-(lower-alkyl)-, heteroaryl, heteroaryl-(lower-alkyl)-, substituted-heteroaryl, (substituted-heteroaryl)-(lower-alkyl)-, heterocyclic, heterocyclic-(lower-alkyl)-, substituted heterocyclic, and (substituted-heterocyclic)-(lower-alkyl)-;

$R^2$ is hydrogen, lower alkyl, amino substituted lower alkyl, lower-alkyl carbonyl, -carboxy-(lower-alkyl), -carbamic acid-(lower-alkyl) and -carboxy-(lower-alkyl)-aryl; and $R^3$ and $R^4$ are independently, hydrogen, lower-alkyl, substituted lower-alkyl, aryl, substituted-aryl, (substituted-aryl)-(lower-alkyl)-, heteroaryl, (heteroaryl)-(lower-alkyl)-, substituted-heteroaryl, (substituted heteroaryl)-(lower-alkyl)-, heterocyclic, heterocyclic-(lower-alkyl)-, substituted-heterocyclic, (substituted-heterocylic)-(lower alkyl)-, -carboxy-(lower-alkyl), and -carboxy-(lower-alkyl)-aryl; or a pharmaceutically acceptable, ester, ether, or salt thereof having somatostatin activity.

An embodiment of the present invention provides compounds of Formula I, as follows,

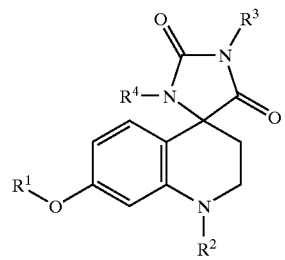

Formula I wherein, $R^1$ is aryl, substituted-aryl, and aryl-(lower-alkyl)-;

$R^2$ is lower alkyl, amino substituted lower alkyl, -carboxy-(lower-alkyl), -carbamic acid-(lower-alkyl) and -carboxy-(lower-alkyl)-aryl; and $R^3$ and $R^4$ are independently, lower-alkyl, aryl, substituted-aryl, (substituted-aryl)-(lower-alkyl)-, heteroaryl, (heteroaryl)-(lower-alkyl)-, substituted-heteroaryl, (substituted heteroaryl)-(lower-alkyl)-, heterocyclic, heterocyclic-(lower-alkyl)-, substituted-heterocyclic, (substituted-heterocylic)-(lower alkyl)-, -carboxy-(lower-alkyl), and -carboxy-(lower-alkyl)-aryl; or a pharmaceutically acceptable, ester, ether, or salt thereof.

Another embodiment of present invention provides a compound of Formula I, as follows,

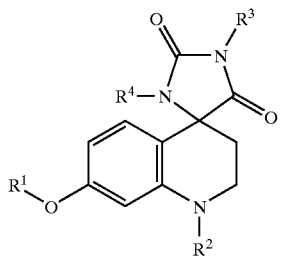

Formula I wherein, $R^1$ is aryl, and aryl-(lower-alkyl)-;

$R^2$ is lower alkyl, amino substituted lower alkyl, -carboxy-(lower-alkyl), -carbamic acid-(lower-alkyl) and -carboxy-(lower-alkyl)-aryl; and $R^3$ and $R^4$ are independently, lower-alkyl, heterocyclic, heterocyclic-(lower-alkyl)-, substituted-heterocyclic, and (substituted-heterocylic)-(lower alkyl)-, or a pharmaceutically acceptable, ester, ether, or salt thereof.

An embodiment of the present invention provides the use of a compound of Formula I for the treatment of diseases and disease states that are effected by somatostatin.

A further embodiment of the present invention provides a compound of Formula II, as follows,

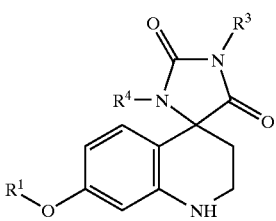

Formula II wherein, $R^1$ is lower-alkyl, substituted lower-alkyl, aryl, substituted-aryl, aryl-(lower-alkyl)-, (substituted-aryl)-(lower-alkyl)-, heteroaryl, heteroaryl-(lower-alkyl)-, substituted-heteroaryl, (substituted-heteroaryl)-(lower-alkyl)-, heterocyclic, heterocyclic-(lower-alkyl)-, substituted heterocyclic, and (substituted-heterocyclic)-(lower-alkyl)-; and $R^3$ and $R^4$ are independently, lower-alkyl, substituted lower-alkyl, aryl, substituted-aryl, (substituted-aryl)-(lower-alkyl)-, heteroaryl, (heteroaryl)-(lower-alkyl)-, substituted-heteroaryl, (substituted heteroaryl)-(lower-alkyl)-, heterocyclic, heterocyclic-(lower-alkyl)-, substituted-heterocyclic, (substituted-heterocylic)-(lower alkyl)-, -carboxy-(lower-alkyl), and -carboxy-(lower-alkyl)-aryl, useful as an intermediate for the preparation of compounds of Formula I.

Another embodiment of the present invention provides a compound of Formula III, as follows,

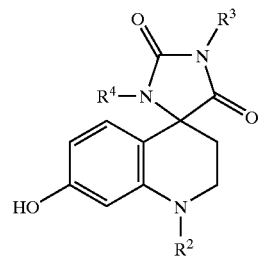

Formula III wherein, $R^2$ is lower alkyl, amino substituted lower alkyl, lower-alkyl carbonyl, -carboxy-(lower-alkyl), and -carboxy-(lower-alkyl)-aryl; and $R^3$ and $R^4$ are independently, lower-alkyl, substituted lower-alkyl, aryl, substituted-aryl, (substituted-aryl)-(lower-alkyl)-, heteroaryl, (heteroaryl)-(lower-alkyl)-, substituted-heteroaryl, (substituted heteroaryl)-(lower-alkyl)-, heterocyclic, heterocyclic-(lower-alkyl)-, substituted-heterocyclic, (substituted-heterocylic)-(lower alkyl)-, -carboxy-(lower-alkyl), and -carboxy-(lower-alkyl)-aryl; useful as an intermediate for the preparation of a compound of Formula I.

Another embodiment of the present invention provides a compound of Formula IV, as follows,

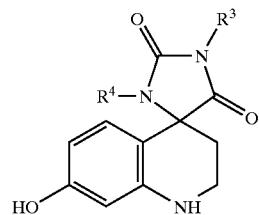

Formula IV wherein, $R^3$ and $R^4$ are independently, lower-alkyl, substituted lower-alkyl, aryl, substituted-aryl, (substituted-aryl)-(lower-alkyl)-, heteroaryl, (heteroaryl)-(lower-alkyl)-, substituted-heteroaryl, (substituted heteroaryl)-(lower-alkyl)-, heterocyclic, heterocyclic-(lower-alkyl)-, substituted-heterocyclic, (substituted-heterocylic)-(lower alkyl)-, -carboxy-(lower-alkyl), and -carboxy-(lower-alkyl)-aryl; useful as an intermediate for the preparation of compounds of Formula I.

A preferred embodiment of the present invention is where $R^1$ is aryl, or substituted-aryl, such as phenyl, and tolyl, respectively.

A preferred embodiment of the present invention is where $R^1$ is -(lower-alkyl)-aryl, such as benzyl.

A preferred embodiment of the present invention is where $R^3$ is lower alkyl substituted with indole, such as indol-3-ylmethyl-, or indol-3-ylethyl; or lower-alkyl, such as methyl.

A preferred embodiment of the present invention is where $R^4$ is lower alkyl substituted with indole, such as indol-3-ylmethyl-, or indol-3-ylethyl; or lower-alkyl, such as methyl.

A preferred embodiment of the present invention is where $R^2$ is -(lower-alkyl)-amine, -(lower-alkyl)-substituted amine, An embodiment of the present invention provides where $R^3$ or $R^4$ is heteroaryl, such as indole, according to the following structure,

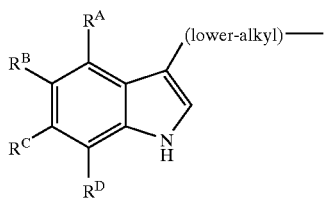

$R^A$, $R^B$, $R^C$, $R^D$ are independently selected from hydrogen, lower alkoxy, halo, and lower alkyl; and attachment is through a lower-alkyl group at the 3-position.

Another embodiment of the present invention provides where $R^3$ or $R^4$ is heteroaryl, specifically pyrimidine, according to the following structure,

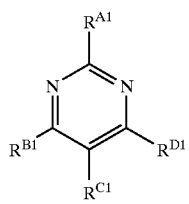

$R^{B1}$, $R^{C1}$, and $R^{D1}$ are independently selected from hydroxy, lower alkyl, amino, lower-alkyl carbonyl lower-alkyl, lower-alkyl-carbamic acid tert-butyl ester, or lower-alkyl carbonyl hydroxyl, and attachment is through a lower-alkyl group at the $R^{A1}$.

Another embodiment of the present invention provides where $R^3$ or $R^4$ are independently substituted monocyclic aryl, or bicyclic heteroaryl selected from the following moieties in Table 1, where "*" indicates the point of attachment.

TABLE 1

| | |
|---|---|
| 3-(2-Oxo-propyl)-2,3-dihydro-isoindol-1-one | 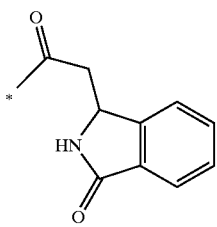 |
| 1-(1H-Benzoimidazol-2-yl)-propan-2-one | 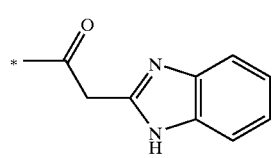 |
| 1-(1,4,5,6-Tetrahydro-cyclopenta-pyrazol-3-yl)-ethanone | 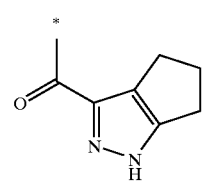 |

TABLE 1-continued

| | |
|---|---|
| 1-(5-Phenyl-2H-pyrazol-3-yl)-ethanone | 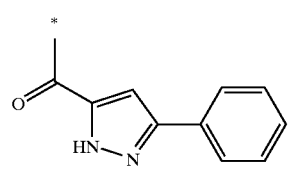 |
| 3-Acetyl-1,3-dihydro-indol-2-one | 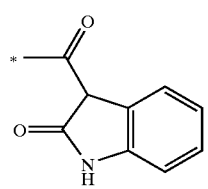 |
| 1-(2-Amino-phenyl)-ethanone | 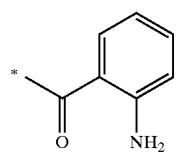 |

Another embodiment of the present invention provides where $R^2$ is selected from the following moieties in Table 2, where "*" indicates the point of attachment.

TABLE 2

| | |
|---|---|
| 7-Amino-heptan-2-one | 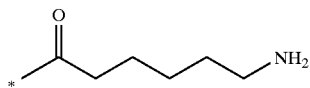 |
| Butylamine | 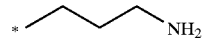 |
| 1-Piperidin-4-yl-ethanone | 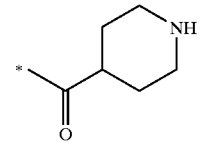 |
| C-(3-Ethyl-cyclohexyl)-methyl amine | 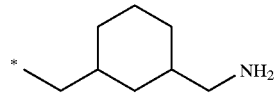 |
| 1-Pyridin-4-yl-ethanone | 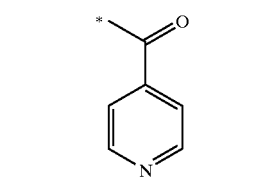 |
| 1-(1,4-Dimethyl-piperazin-2-yl)-propan-2-one | 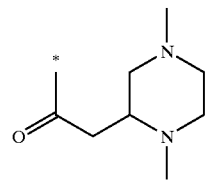 |

TABLE 2-continued

| | |
|---|---|
| 4-Acetyl-pyrrolidin-2-one | 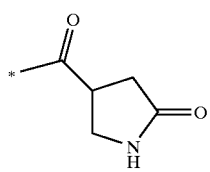 |
| 4-Ethyl-pyrrolidin-2-one | 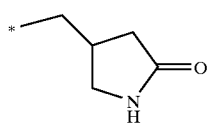 |
| 1-Azetidin-2-yl-ethanone | 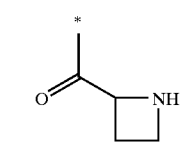 |
| 1-Pentyl-piperidine | 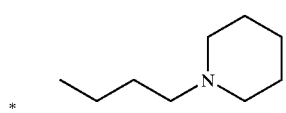 |
| 4-Pentyl-morpholine | 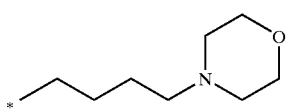 |
| 1-Pentyl-piperazine | 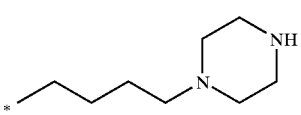 |
| 1-Pentyl-1H-imidazole | 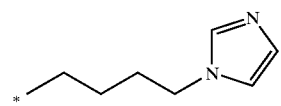 |
| 1-[1,2,4]Triazol-1-yl-propan-2-one | 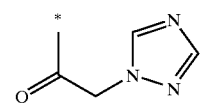 |
| 1-(1H-Imidazol-2-yl)-propan-2-one | 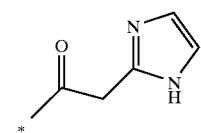 |

There are relatively few examples of the use of clearly defined general methods that allow for the design and preparation of compounds that would be useful for the general exploration of the numerous potential combinatorial pharmacophoric possibilities that do not include α-amino acids in the scaffold. One early notable example of such an approach is that of Hirschmann and co-workers (Hirschmann, R.; Nicolaou K. C.; Pietranico, S.; Leahy, E. M.; Salvino, J.; Arison, B.; Cichy M. A.; Spoors, P. G.; Shakespeare, W. C.; Sprengler, P. A.; Hamley, P.; Smith, A. B. III, Reisine, T.; Raynor, K.; Maechler, L.; Donaldson, C.; Vale, W.; Freidinger, R. M.; Cascieri, M. R.; Strader, C. D., De novo Design and Synthesis of Somatostatin Non-peptide Peptidomimetics Utilizing Beta-D-glucose as a Novel Scaffolding. *J. Am. Chem. Soc.* 1993, 115, 12550–12568).

Recently, Garland and Dean (Garland S. L.; Dean P. M., Design Criteria for Molecular Mimics of Fragments of the β-Turn. 1. Cα Atom Analysis. *J. Comp. Aided Mole. Des.* 1999, 13, 469–483.) reported that cluster analysis and recombination of the observed patterns yielded a consensus positioning of the C-α atoms among the various beta-turn types. They showed that this relationship could be visualized as three independent specific three-point (triangular) distance-geometries that are common to all beta-turn types. They also demonstrated that these triangles could be used as queries to search 3D databases and find existing compounds that match the consensus positioning of the C-α atoms of beta-turns. Garland and Dean demonstrated the utility of this approach as a screen for existing compounds that possess the rather rare combination of a very specific constrained atomic positioning required to mimic the main-chain positioning observed in beta turns, and the capacity for the synthetic introduction of the required groups to mimic the side chain interactions.

Expanding on the Garland-Dean approach, it may be possible to construct other scaffolds that are suitable for the exhibition of many combinatorial pharmacophoric possibilities that may be observed in bioactive peptides.

The present invention provides the following novel scaffolds, Match Type I, II, and III, which contain multiple substitution points that match several of the Garland-Dean geometries.

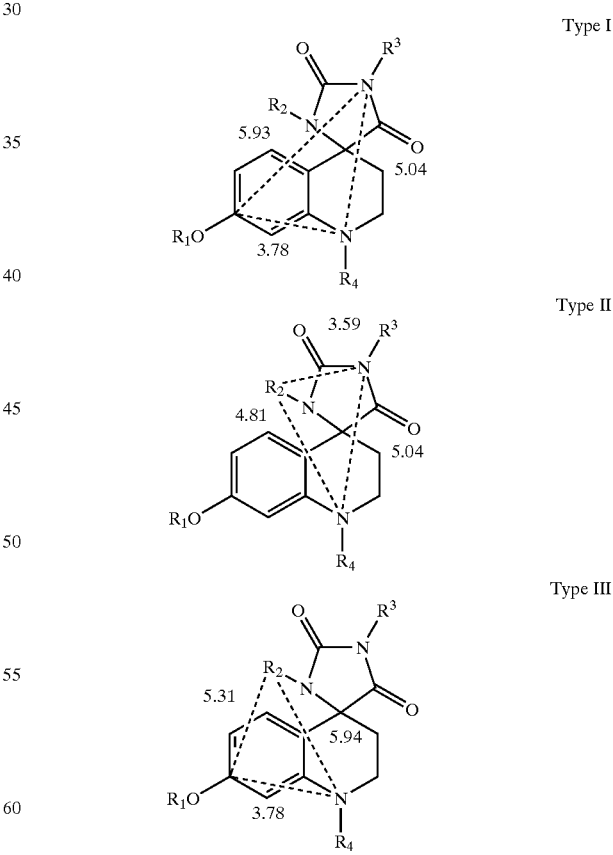

The present invention does not include any α-amino acids in the scaffolds since such compounds usually do not have the desired physical properties. The compounds of the present invention are based on the scaffolds of Figure 1.

DETAILED DESCRIPTION

Definitions:

The following definitions, are set forth to illustrate and define the meaning and scope of the various terms used to describe the invention herein.

As used herein, the term "alkyl" refers to a branched or straight chain monovalent saturated aliphatic hydrocarbon radical of one to twenty carbon atoms. As used herein, the term "lower-alkyl" refers to a branched or straight chain monovalent alkyl radicals of one to seven carbon atoms. This term includes, but is not limited to such radicals as methyl, ethyl, propyl, butyl, pentyl, hexyl, and heptyl; and in the instances where there are three or more carbons, the various isomeric forms for each radical. For example, butyl includes, iso-butyl, n-butyl, and tert-butyl; or propyl includes, n-propyl, and iso-propyl.

As used herein, the term "substituted lower-alkyl" refers to a monovalent carbocyclic radical of three to seven carbon atoms, which can optionally be mono-, di-, or tri-substituted, independently, with hydrogen, hydroxyl, amino, halo, nitro, lower-alkoxy, mono-lower-alkylamino, di-lower-alkylamino, hydroxycarbonyl, lower-alkoxycarbonyl, carbamoyl, lower-alkylcarbamoyl, and di-lower-alkylcarbamoyl.

As used herein, the term "lower alkoxy" refers to the radical —O—R' where R' is lower alkyl.

As used herein, the term "methylene" refers to the radical —CH$_2$—.

As used herein, the term "carbonyl" refers to the radical —C(O)—, alternatively, this functional group can also be referred to as "oxo."

As used herein, the terms "hydroxycarbonyl," "carboxy," or "carboxylic acid" refers to the radical —C(O)OH.

As used herein, the term "lower-alkoxycarbonyl" refers to the radical —C(O)OR' where R' is lower-alkyl.

As used herein, the term "acyl" refers to the radical —C(O)—R', where R' is lower-alkyl, e.g., methylcarbonyl and ethylcarbonyl.

As used herein, the term "carbamoyl" refers to the radical —C(O)NR'R where R and R' are independently hydrogen or lower-alkyl, e.g., where R is hydrogen and R' is lower-alkyl the group is lower-alkylcarbamoyl, where R and R' are lower-alkyl the group is di-lower-alkylcarbamoyl.

As used herein, the term "halo" refers to fluoro, bromo, chloro or iodo.

As used herein, the term "phenyl" or "Ph-" refers to a benzene radical.

As used herein, the term "phenoxy" refers to the radical "Ph-O—."

As used herein, the term "benzyl" or "Bn—" refers to a (—CH$_2$-phenyl) radical.

As used herein, the term "benzoxy" refers to a —O-Benzyl radical.

As used herein, the term "aryl" refers to an aromatic monovalent mono- or poly-carbocyclic radical.

As used herein, the term "substituted aryl," refers to an aromatic monovalent mono- or poly-carbocyclic radical, which can optionally be mono-, di-, or tri-substituted, independently, with hydrogen, hydroxyl, amino, halo, nitro, lower-alkoxy, mono-lower-alkylamino, di-lower-alkylamino, hydroxycarbonyl, lower-alkoxycarbonyl, carbamoyl, lower-alkylcarbamoyl, and di-lower-alkylcarbamoyl.

As used herein, the term "aryl lower-alkyl" refers to the group aryl-(lower alkyl)-, where the lower-alkyl moiety connects the aryl moiety to another moiety. For example, typical aryl lower alkyl groups are naphalenyl lower-alkyl, phenylethyl, phenylmethyl (also known as benzyl). Similarly, the term "substituted aryl lower-alkyl" refers to the analogous structure where the aryl group is substituted as previously taught.

As used herein, the term "heteroaryl" refers to an aromatic monovalent mono- or poly-carbocyclic radical having at least one heteroatom (i.e., nitrogen, oxygen or sulfur), where the radical optionally can be mono- or di-substituted, independently, with lower alkyl, halo, cyano, amino or trifluoromethyl. As used herein, the term "N-heteroaryl" refers to a heteroaryl radical having at least one nitrogen atom. For example, typical N-heteroaryl groups with one or more nitrogen atoms are tetrazolyl, pyridyl (e.g., 4-pyridyl, 3-pyridyl, 2-pyridyl), pyridazinyl, quinolinyl, 2-quinolinyl, 3-quinolinyl, imidazolyl, isoquinolinyl, pyrazolyl, pyrazinyl, pyrimidinyl, pyridonyl or pyridazinonyl; typical oxygen heteroaryl radicals are furanyl, or benzofuranyl; typical sulfur heteroaryl radicals are thienyl and benzothionyl.

As used herein, the term "substituted heteroaryl" refers to a heteroaryl radical which can optionally be mono-, di-, or tri-substituted, independently, with hydrogen, hydroxyl, amino, halo, nitro, lower-alkoxy, mono-lower-alkylamino, di-lower-alkylamino, hydroxycarbonyl, lower-alkoxycarbonyl, carbamoyl, lower-alkylcarbamoyl, and di-lower-alkylcarbamoyl.

As used herein, the term "heteroaryl lower-alkyl" refers to the group -(lower alkyl)-(heteroaryl), where the lower-alkyl moiety connects the heteroaryl moiety to another group. For example, typical heteroarylalkyl groups are pyridyl-lower alkyl, such as, pyridylmethyl (e.g., 4-pyridylmethyl, 3-pyridylmethyl and 2-pyridylmethyl), pyridylethyl, pyridylpropyl, pyridylbutyl, quinolinyl-lower alkyl, furanyl-lower alkyl, and pyridonyl-lower alkyl. As used herein, the term "heteroarylmethyl" refers to the radical —CH$_2$—(heteroaryl). Similarly, the term "substituted heteroaryl lower-alkyl" refers to analogous structures where the heteroaryl group is substituted as previously taught.

As used herein, the term "heterocyclic" refers to a monovalent mono- or poly- carbocyclic radical having at least one heteroatom (i.e., nitrogen, oxygen or sulfur), where the radical is optionally saturated or unsaturated, and optionally can be mono- or di-substituted, independently, with —H, lower alkyl, halo, cyano, amino or substituted amino. As used herein, the term "N-heterocyclic" refers to a heterocyclic radical with one, or more nitrogen atoms, such as indole, pyrrolidinyl, piperidinyl, azepanyl, pyrazolyl, or imidazolyl.

As used herein, the term "substituted heterocyclic" refers to a heterocyclic monovalent mono- or polycyclic radical, which can optionally be mono-, di-, or tri-substituted, independently, with hydrogen, hydroxyl, amino, halo, nitro, lower-alkoxy, mono-lower-alkylamino, di-lower-alkylamino, hydroxycarbonyl, lower-alkoxycarbonyl, carbamoyl, lower-alkylcarbamoyl, and di-lower-alkylcarbamoyl.

As used herein, the term "heterocyclic lower-alkyl", refers to the group "heterocyclic-(lower-alkyl)-," where the lower-alkyl moiety connects the heterocyclic group to another group. Similarly, the term "substituted heterocyclic lower-alkyl" refers to analogous structures where the heterocyclic moiety is substituted as previously taught.

As used herein, the term "pharmaceutically acceptable esters" refers to those compounds formed from compounds of Formula I containing a carboxy group when contacted with an alcohol, such as, methanol, ethanol or propanol under suitable conditions.

As used herein, the term "pharmaceutically acceptable ethers" refers to those compounds formed from compounds of Formula I containing a hydroxy group when contacted with a suitable reagents (e.g., alkyl halide) under suitable conditions.

As used herein, the term "esterification reagent" refers to a reagent (e.g., diazomethane, methanol, methyl iodide, ethyl iodide or ethanol) that when contacted with a carboxy group under suitable circumstances results in the formation of the corresponding alkoxycarbonyl group.

As used herein, the term "pharmaceutically acceptable salt" refers to any salt derived from an inorganic or organic acid or base.

As used herein, the term "compound", as used in the detailed description and in the claims in reference to a compound of Formula I, is intended to refer to the pharmaceutically acceptable salts, esters, or ethers of the compound, unless expressly stated otherwise, such as "the compound of Formula I as a free base".

As used herein, the term "pharmaceutically acceptable anion" refers to the anion of such acid addition salts. The term "pharmaceutically acceptable cation" refers to the cation of such base addition salts. The salt, anion and/or the cation are chosen not to be biologically or otherwise undesirable. The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like. The cations are derived from bases, such as alkaline earth hydroxides, including calcium hydroxide, potassium hydroxide, sodium hydroxide, lithium hydroxide and the like.

As used herein, the terms "treatment" or "treating" of a condition and/or a disease in a mammal, including humans means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms. The conditions and diseases treated in the present invention include, inflammation, pain.

As used herein, the term "therapeutically effective amount" refers to that amount of a compound of Formula I which, when administered to a mammal in need thereof, is sufficient to effect treatment (as defined above) as an anti-inflammatory agent, analgetic agent (i.e., pain relieve). The amount that constitutes a "therapeutically effective amount" will vary depending on the compound, the condition or disease and its severity, and the mammal to be treated, but may be determined routinely by one of ordinary skill in the art with regard to contemporary knowledge and to this disclosure.

As used herein the term "agonist" refers to an agent, such as, a chemical compound, that when exposed to a receptor elicits an agonist response, that is, the maximal normal biological response of the endogenous ligand binding to the receptor is duplicated.

As used herein the term "antagonist" refers to an agent, such as, a chemical compound, that when exposed to a receptor binds with the receptor, but does not elicit a biological response. An antagonist can block an agonist response by occupying the receptor thereby preventing the agonist from binding with the receptor. This type activity is referred to as competitive antagonism, or competitive inhibiton. The activity of a competitive antagonist can be overcome by increasing the amount of agonist. An antagonist can also block an agonist response by binding at a site other than the receptor. This type of activity is referred to as non-competitive antagonism, or non-competitive inhibition. The activity of a non-competitive antagonist is not overcome by increasing the concentration of the agonist.

As used herein the term "partial agonist" refers to an agent, such as, a chemical compound, that when exposed to a receptor elicits a response, however, the maximum response obtained is less than that of another agonist, such as the physical ligand. A partial agonist can act both as an agonist or antagonist depending on the setting. For example, a partial agonist in the absence of the natural agonist can act as an agonist by eliciting a partial agonist response. Conversely, a partial agonist in the presence the natural agonist can act as an antagonist by competing with the natural agonist for binding with the receptors, thereby decreasing the overall agonist response.

As used herein the term "$IC_{50}$" or "inhibitory concentration" refers to the dose or concentration of an antagonist of an agent, such as a chemical compound, to achieve 50% of inhibition of biological activity; or the dose or concentration to achieve 50% of maximal binding.

As used herein the term "$EC_{50}$" refers to the dose or concentration of an agonist to achieve 50% of maximum activity, that is, agonist response; or the dose or concentration of an agonist to produce a response in 50% of the subjects tested.

As used herein, the term "mp" refers to melting point. All temperatures are given in degrees Celsius (i.e., ° C.)

Unless specified to the contrary, the reactions described herein take place at atmospheric pressure over a temperature range from about −78° C. to about 150° C., more preferably from about 10° C. to about 50° C., and most preferably at about room (or "ambient") temperature, e.g., about 20° C. Unless specified to the contrary, the ranges of time and temperature described herein are approximate, e.g., "from 8 to 24 hours at from 10° C. to 100° C." means from about 8 to about 24 hours at about 10° C. to about 100° C.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples herein. However, other equivalent separation or isolation procedures can also be used.

The following numbering and nomenclature system will be used for naming the compounds of the invention.

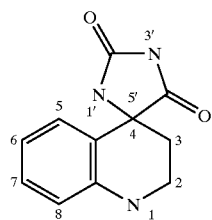

The positions of the quinoline moiety of the present invention are identified with unprimed number. The positions of the imidazoline-2,4-dione moiety of the present invention are identified with primed numbers. It should be noted that because of the Spiro union between the two ring moieties, position 4 of the quinoline ring designates the same atom as position 5' of the imidazoline-2,4-dione ring.

Some representative compounds are named in the following examples.

For example, the compound of Formula I taught in Example 8, where $R^1$ is phenyl, $R^2$ is carboxylic acid benzyl ester, and $R^3$ and $R^4$ are H, that is,

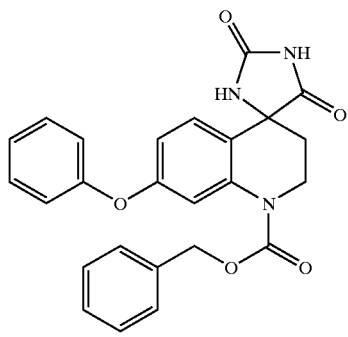

can be named 7-phenoxy-3,4-dihydro-2H-quinoline-1-carboxylic acid benzyl ester-4-spiro-5'-imidazoline-2',4'-dione.

For example, the compound of Formula I taught in Example 16 where $R^1$ is phenyl, $R^2$ is carboxylic acid benzyl ester, $R^3$ is methyl and $R^4$ are H,

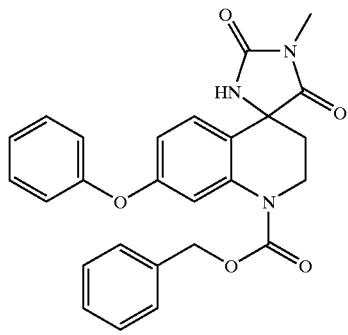

can be named, 7-Phenoxy-3,4-dihydro-2H-quinoline-1-carboxylic acid benzyl ester-4-spiro-5'-3'-methyl-imidazoline-2',4'-dione.

For example, the compound of Formula I taught in Example 21, where $R^1$ is phenyl, $R^2$ is 4-butylamine, $R^3$ is methyl, and $R^4$ is 1H-indol-3-ylmethyl, that is,

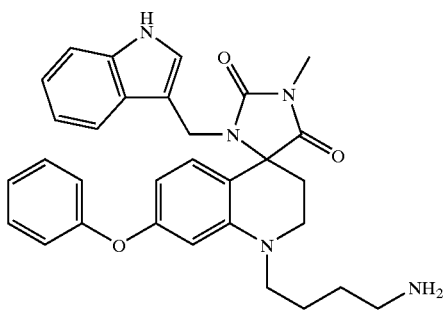

can be named, 7-phenoxy-3,4-dihydro-2H-quinoline-1-(4-butylamine)-4-spiro-5'-1'-(1H-indol-3-ylmethyl)-3'-methyl-imidazoline-2',4'-dione.

Preparation of the Compounds of Formula I

Starting materials for most of the compounds illustrated in the following reaction schemes are commercially available from various commercial entities, such as, Aldrich Chemicals Inc., Fluka Chemical Corporation.

Those compounds that are not commercially available can be prepared by one of ordinary skill in art following procedures set forth in references such as, "Fieser and Fieser's Reagents for Organic Synthesis", Volumes 1–15, John Wiley and Sons, 1991; "Rodd's Chemistry of Carbon Compounds", Volumes 1–5 and Supplementals, Elservier Science Publishers, 1989; and "Organic Reactions", Volumes 1–40, John Wiley and Sons, 1991.

Reaction Scheme A illustrates the preparation of novel optionally substituted-3,4-dihydro-2H-quinoline-4-spiro-5'-imidazoline-2',4'-diones, i.e., the compounds of Formula I

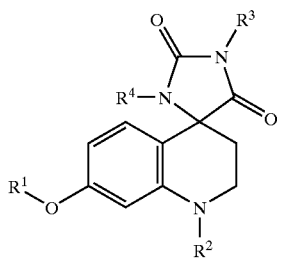

where, $R^1$ is lower-alkyl, substituted lower-alkyl, aryl, substituted-aryl, heteroaryl, substituted-heteroaryl, heterocyclic, and substituted heterocyclic;

$R^2$, $R^3$ and $R^4$ are, independently, hydrogen, aryl, substituted aryl, heteroaryl, substituted-heteroaryl, heteroarylmethyl, substituted-heteroarylmethyl, heterocyclic, substituted heterocyclic, lower-alkoxy carbonyl, aryloxy carbonyl, substituted aryloxy carbonyl, substituted aryl lower-alkoxy carbonyl; or a pharmaceutically acceptable, ester, ether, or salt thereof.

Reaction Scheme A

Preparation of Compound 1

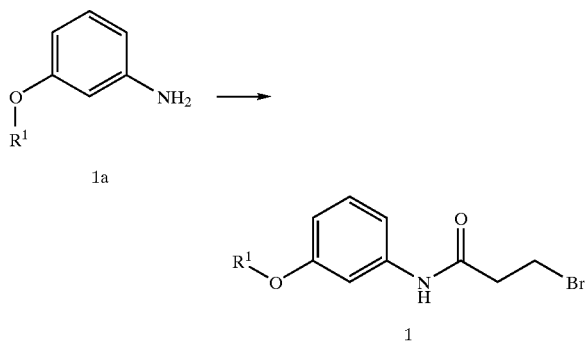

An optionally substituted-oxy-phenylamine 1a (where $R^1$ is aryl, lower-alkyl aryl, lower alkyl) is treated successively with about 1 molar equivalent of 3-phenoxyaniline in a suitable nonpolar solvent, such as, dichloromethane, about 1 molar equivalent of 1-(3-dimethyl-aminopropyl)-3-ethylcarbodiimide HCl, and about 0.05 molar equivalent of 4-dimethylaminopyridine under a dry and inert atmosphere. The resulting solution was stirred for about 30 minutes at about room temperature. The mixture was purified by extraction using a succession of acid, base and brine washes. The resultant material is dried and used directly in the preparation of Compound 2.

Preparation of Compound 2

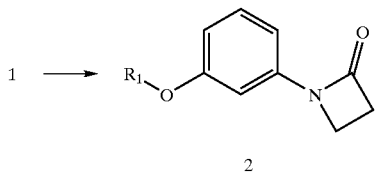

A beta lactam of Compound 2 (where $R^1$ is aryl, lower-alkyl aryl, lower alkyl) is prepared by dissolving Compound 1 in an appropriate volume of a suitable nonpolar solvent, such as, dichloromethane, and treated successively with about 1 molar equivalent of a strong base, such as, KOH, and about 1 molar equivalent of a strong quaternary ammonium base, such as, tetrabutyl-ammonium bromide. The combined solution is stirred for about 3 hours at about room temperature. The desired product is concentrated from the reaction solution by succesive extractions with a suitable polar solvent, such as, water, a suitable base solution, such as, $NH_4Cl$, and brine. The resulting residue is purified by standard chromatographic procedures, such as column chromatography, or the like.

Preparation of Compound 3

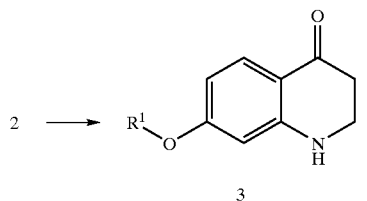

Compound 3 (where $R^1$ is aryl, lower-alkyl aryl, lower alkyl) is prepared by performing an amino ketone cyclization on Compound 2. Compound 2 is dissolved in a suitable nonpolar solvent, such as, dichloromethane, and treated with a selective base reagent, such as, polyphosphoric ester, under a dry inert atmosphere. The combined solution was stirred and refluxed for about 1.5 hours. The reaction solution was concentrated by evaporation, and added to a ice/water solution. This solution was extracted through a series of nonpolar solvent washes, such as, ethyl acetate, and polar solvent washes, such as, sat. aqueous $NaHCO_3$ and brine. The resultant material was purified using standard chromatographic procedures, such as, column chromatography.

Alternatively, Compound 3 is prepared by treating a solution of Compound 2 with strong acid, such as, trifluoroacetic acid, and refluxing the combined solution with stirring for about 1 hour, under a dry inert atmosphere. The reaction solution is diluted with a mixture of ice and water, treated with a base, such as sat. aqueous $NH_3$, and extracted with successive washes with a suitable nonpolar solvent, such as, chloroform, or dichloromethane. The resulting material is dried, concentrated by evaporation, and purified by standard chromatographic techniques, such as, column chromatography.

Preparation of Compound 4

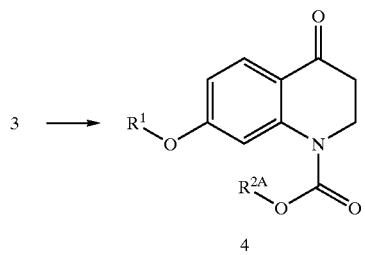

Compound 4 (where $R^1$ is aryl, lower-alkyl aryl, lower alkyl; and $R^{2A}$ is aryl, or lower-alkyl aryl) is prepared by adding Compound 3 to a suitable nonpolar solvent, such as dichloromethane, containing about 4 molar equivalent of alkyl ammonium base, such as diisopropylethylamine, to which is added in a gradual manner, such as dropwise, about 3 molar equivalent of benzyl chloroformate under a dry inert atmosphere. The reaction solution was stirred for about 48 hours. The solution is then diluted about one and a half fold with a suitable nonpolar solvent, and washed with successive rinse of water, 1N acid, such as HCl, sat. aqueous base, such as $NaHCO_3$, dried and concentrated by evaporation. The resultant material is purified using standard chromatographic procedures, such as column chromatography.

Preparation of Compound 5

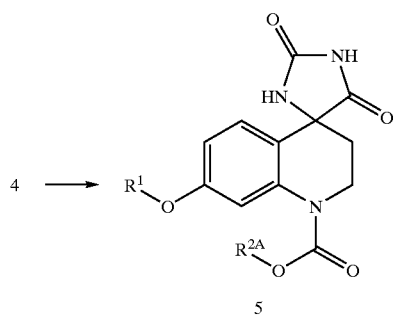

Compound 5 (where $R^1$ is aryl, lower-alkyl aryl, lower alkyl; and $R^{2A}$ is aryl, or lower-alkyl aryl) is prepared by adding Compound 4 to a suitable polar solvent, such as absolute ethanol, or 95% ethanol solution, preferably, 95% ethanol, and treating the solution with about 10 to 20, preferably about 10 molar equivalent of ammonium carbonate, and about 4 molar equivalent of potassium cyanide. The reaction solution was heated in a seal pressure tube for about 72 hours and then poured into cold aqueous HCl, and extracted with a polar solvent, such as ethyl acetate. The combined extracts were dried, and concentrated by evaporation, and purified using standard chromatographic procedures, such as column chromatography. Compound 5 is a useful intermediate in the preparation of the compounds of Formula I. Compound 5 is suitable for the step-wise regioselective introduction of desired moieties at $R^3$ and $R^4$.

Preparation of Compound 6

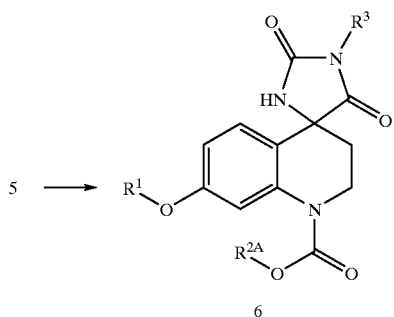

Compound 6 (where $R^1$ is aryl, lower-alkyl aryl, lower alkyl; $R^{2A}$ is aryl, or lower-alkyl aryl; and $R^3$ is lower-alkyl, lower-alkyl aryl, heteroaryl, substituted-heteroaryl) is prepared by treating Compound 5 with alkylating agents, such as those taught in Reaction Schemes B. Compound 5 is dissolved in a suitable polar solvent, such as dimethylformamide, and was treated with about 2 molar equivalent of cesium bicarbonate, and about 1.5 molar equivalent of an optionally substituted alkylating agent, $R^3$—X (where $R^3$ is lower-alkyl, lower-alkyl aryl, heteroaryl, lower-alkyl heteroaryl, substituted-heteroaryl; and X is a suitable leaving group, such as —Cl, —Br, or —I). The reaction solution is stirred under an inert atmosphere and heated to about 60° C. for about 12 hours. The solution is allowed to cool to about room temperature, and added to a saturated aqueous base solution, such as $NH_4Cl$. The solution is then extracted with an appropriate nonpolar organic solvent, such as ethyl acetate. The collected extracts were washed with water, brine, dried and concentrated by evaporation resulting in Compound 6. The resulting material is purified by standard chromatographic procedures to yield Compound 6.

Preparation of Compound 7

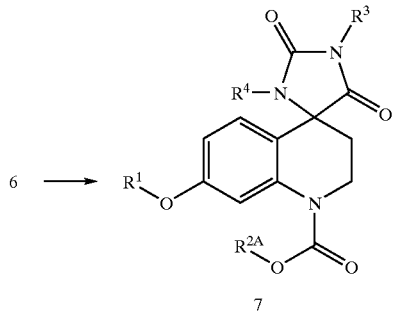

Compound 7 (where $R^1$ is aryl, lower-alkyl aryl, lower alkyl; $R^{2A}$ is aryl, or lower-alkyl aryl; and $R^3$ and $R^4$ are independently, lower-alkyl, lower-alkyl aryl, heteroaryl, lower-alkyl heteroaryl, substituted-heteroaryl) is prepared by treating Compound 6 with site specific alkylating agents, such as those taught in Reaction Schemes B. Compound 6 is dissolved in a suitable polar solvent, such as dimethylformamide, and is treated with about 2 molar equivalent of potassium carbonate and about 1.5 molar equivalent of an optionally substituted alkylating reagent, $R^4$—X (where $R^4$ is lower-alkyl, lower-alkyl aryl, heteroaryl, lower-alkyl heteroaryl, substituted-heteroaryl; and X is a suitable leaving group, such as —Cl, —Br, and —I). The reaction solution is stirred for about 18 hours in a seal vessel at about room temperature. The reaction solution is combined with a mild aqueous acid, such as $NH_4Cl$, then extracted with a suitable nonpolar organic solvent, such as ethyl acetate. The combined extracts are washed with water, brine, dried and concentrated by evaporation. The resulting material is purified by standard chromatographic procedures to yield Compound 7.

Preparation of Compound 8

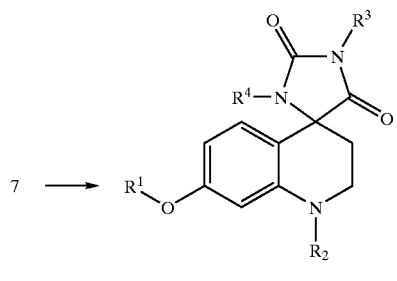

Compound 8 (where $R^1$ is aryl, lower-alkyl aryl, lower alkyl; $R^2$ is hydrogen; and $R^3$ and $R^4$ are independently, lower-alkyl, lower-alkyl aryl, heteroaryl, substituted-heteroaryl) is prepared by combining Compound 7 with about 5 molar equivalent of ammonium formate in a suitable polar protic solvent, such as methanol, in a sealed reaction vessel. The solution is treated with a catalytic amount of a reducing agent, such as 10% palladium on charcoal. The reaction mixture is stirred at about 60° C. for about one hour. The resulting material is filtered, and washed with a suitable polar solvent, such as methanol. The material is further purified by standard chromatographic procedures yielding the desired Compound 8.

Preparation of Compound 9

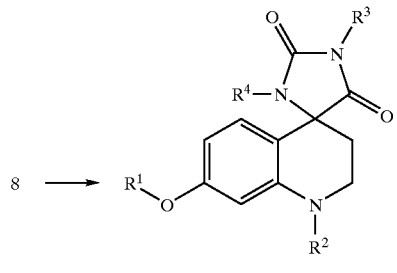

Formula I

Formula I (where $R^1$ is aryl, lower-alkyl aryl, lower alkyl; $R^2$ is lower heteroalkyl, lower alkylaryl, cyclic lower-alkyl, lower-heteroalkylaryl; and $R^3$ and $R^4$ are independently, lower-alkyl, lower-alkyl aryl, heteroaryl, lower-alkyl heteroaryl, substituted-heteroaryl or lower-alkyl substituted heteroaryl.

Regiospecific alkylation at the 3' position versus the 5' position is generally accomplished by taking advantage of the stronger acidity of this nitrogen atom. Thus, treatment of Compound 5 with a weak base, such as CsHCO$_3$ specifically deprotonates the 3' NH to give a reactive anion. Subsequently a stronger base, such as NaH can be used to deprotonate the 1' NH so that this position can be alkylated.

Utility, Testing and Administration General Utility

The compounds of the present invention, including the pharmaceutically acceptable salts, esters and ethers thereof, and the compositions containing them are particularly useful in the treatment of numerous disease states such as acromegaly, diarrhea associated with cancer, cancer, pain associated with cancer, diabetes, and epilepsy.

Somatostatin (SST) is a widely distributed peptide occurring in the central nervous system and peripheral tissues such as stomach, intestine, and pancreas and exerts its biologic effects by binding to specific high-affinity receptors, which appear in many cases to be coupled to GTP-binding proteins. SST occurs in two forms SST-14 (with 14 amino acids) and SST-28 (with 28 amino acids). SST has multiple functions including modulation of secretion of growth hormone, insulin, glucagon, pancreatic enzymes and gastric acid, in addition to having potent anti-proliferative effects.

The mechanism of action of SST is mediated via high affinity membrane associated receptors. To date, five somatostatin receptors (SSTR1–5) have been identified, (Reisine, T.; Bell, G. I. Endocrine Reviews 1995, 16, 427–442). All five receptors are heterogeneously distributed and pharmacologically distinct. The availability of these receptors makes it possible to design selectively active ligands for the sub-types to determine their physiological functions and to guide potential clinical applications. For example, studies utilizing subtype selective peptides have provided evidence that somatostatin subtype 2 receptors sst2 mediates the inhibition of growth hormone release from the anterior pituitary and glucagon release from the pancreas, whereas sst5 selective agonists inhibit insulin release.

The compounds and compositions of the present invention act as somatostatin agonists, partial agonists, or antagonists thereby making them useful as pharmacologic agents for mammals, especially for humans, for the treatment and prevention of disorders wherein somatostatin itself or the hormones it regulates may be involved. Examples of such disorders include diabetes, acromegalym neuropathic pain, restenosis, retinopathy, depression, arthritis, cancer and cancer associated pain.

The compounds and compositions of the present invention are useful for modulation of the activity of G-protein coupled receptors (GPCRs), particularly those that are associated with the onset of cancer.

The instant compounds inhibit cell proliferation and cause the regression of certain tumors including breast cancer. They are useful in preventing restenosis after angioplasty, they prevent non-steroid anti-inflammatory drug (NSAID) induced ulcers, they are useful in treating colitis and inhibit cystoid macular edema. Their central activities include promotion of REM sleep and increasing cognitive function. They also have analgesic activities and can be used, for example, to treat cancer pain, cluster headache and post operative pain. They are useful in the prevention and treatment of migraine attacks and depression. The compounds and compositions described herein may be used in combination with other therapies, for example, with rapamycin to treat cancers, restenosis and atherosclerosis and with angiotensin converting enzyme inhibitors and insulin in the treatment of diabetes. The compounds of this invention are significantly smaller in size in comparison with the natural hormone and its peptide analogs, such as octreotide and seglitide. This provides compounds that are easier to formulate.

The compounds and compositions described herein are useful in the therapy of a variety of conditions which include acromegaly, retinal neovascularization, neuropathic and visceral pain, irritable bowel syndrome, chronic atrophic gastritis, Crohn's disease, rheumatoid arthritis and sarcoidosis, and nausea and vomiting, that is as anti-emetic agents.

Somastostatin in the brain inhibits the neuronal release of substance P(NK-1) and NK-1 antagonists have been shown to have a marked use as an antidepressant agent. Accordingly, the present invention is also useful in treating depression.

The compounds and compositions of the present invention can be used to inhibit the secretion of various hormones and trophic factors in mammals. For example, the present invention can be used to, suppress certain endocrine secretions, such as GH, insulin, glucagon and prolactin; in the treatment of disorders such as acromegaly; endocrine tumors such as carcinoids, vipomas, insulinomas and glucagonomas; or diabetes and diabetes-related pathologies, including retinopathy, neuropathy and nephropathy. The present invention may also be used to suppress exocrine secretions in the pancreas, stomach and intestines, for treatment of disorders such as pancreatitis, fistulas, bleeding ulcers and diarrhea associated with such diseases as AIDS or cholera.

The compounds and compositions of the present invention can be used to suppress the mediators of neurogenic inflammation, for example, substance P or the tachykinins, and can be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving the splanchnic blood flow, including cirrhosis and oesophagal varices, the compounds of the invention can provide cytoprotection.

The ability of the compounds of the present invention to act as somatostatin agonists makes them useful as pharmacologic agents for mammals, especially for humans, for the treatment and prevention of disorders wherein somatostatin itself or the hormones it regulates may be involved. Examples of such disorders have been noted earlier and include diabetes, acromegaly, neuropathic pain, restenosis, arthritis and cancer, in particular, breast cancer. The instant compounds can also be used in combination with other therapeutic agents. For example, for the treatment of breast cancer these agents include tamoxifen.

The present invention can be used in combination with other therapeutic agents which are useful for treating the aforementioned conditions. For example, for the treatment of breast cancer, agents including but not limited to aredia (pamidronate disodium), arimidex (anastrozole), aromasin (exemestane), ellence (epirubicin hydrochloride), fareston (toremifene citrate), femara (letrozole), herceptin (trastuzumab), nolvadex (tamoxifen citrate), taxol (paclitaxel), taxotere (docetaxel), and xeloda (capecitabine), can be used in combination with the present invention. In the instance of prostrate cancer, agents including but not limited to lupron depot (leuprolide acetate), nilandron (nilutamide), novantrone (mitoxantrone hydrochloride), trelstar depot (triptorelin palmoate), viadur (leuprolide acetate implant), and zoladex (goserelin acetate implant). For example, for diabetes treatment agents such as metformin or other biguanides, acarbose, sulfonylureas, thiazolidinediones or other insulin sensitizers including, but not limited to, compounds which function as agonists on peroxisome proliferator-activated receptor gamma (PPAR-gamma), insulin, insulin-like-growth factor I, glucagon-like peptide I-glp-I and available satiety-promoting agents such as dexfenfluramine, can be used in combination with the present invention.

Testing

Compounds of the present invention were assessed for their binding affinity to sst1, sst3, and sst4 receptors by biochemical and radioligand assay according to the following procedures. The assays were conducted by MDS Pharma Services—Taiwan Ltd., Pharmacology Laboratories, 158 Li-The Road, Peitou, Taipei, Taiwan 112, R.O.C.

The protocol for sst1 assay was adapted from Liapakis, G., Fitzpatrick, D., Hoeger, C., Rivier, J., Vandlen, R. and Reisine, T. (1996) "Identification of ligand binding determinants in the somatostatin receptor subtypes 1 and 2."*J. Biol. Chem.* 271(24): 20331–20339, 1996; and Patel, Y. C. and Srikant, C. B. (1994) "Subtype selectivity of peptide analogs for all five cloned human somatostatin receptors (hsstr 1–5)." *Endocrinology* 135 (6): 2814–2817, 1994. The protocol were and can be conducted according to the following conditions.

| Somatostatin sst1 | |
|---|---|
| Source: | Human recombinant CHO-K1 |
| Ligand: | 0.1 nM $^{125}$I Somatostatin-14 |
| Vehicle: | 0.4% DMSO |
| Incubation Time/Temp: | 2 hours at 25° C. |
| Incubation Buffer: | 50 nM Hepes, pH 7.4, 5 mM $MgCl_2$ 1 mM $CaCl_2$, 0.5% BSA |
| NonSpecific Ligand: | 1 µM Somatostatin-14 |
| $K_d$: | 1.9 nM* |
| $B_{max}$: | 1.5 pmol/mg Protein* |
| Specific Binding | 60%* |
| Quantitation Method: | Radioligand Binding |
| Significance Criteria: | ≧50% of max stimulation or inhibition |

*historical values

The protocol for sst3 assay was adapted from Liapakis, G., Fitzpatrick, D., Hoeger, C., Rivier, J., Vandlen, R. and Reisine, T. (1996) "Identification of ligand binding determinants in the somatostatin receptor subtypes 1 and 2."*J. Biol. Chem.* 271(24): 20331–20339, 1996; and Patel, Y. C. and Srikant, C. B. (1994) "Subtype selectivity of peptide analogs for all five cloned human somatostatin receptors (hsstr 1–5)." *Endocrinology* 135 (6): 2814–2817, 1994. The protocol were and can be conducted according to the following conditions.

| Somatostatin sst 3 | |
|---|---|
| Source: | Human recombinant CHO-K1 |
| Ligand: | 0.1 nM $^{125}$I Somatostatin-14 |
| Vehicle: | 0.4% DMSO |
| Incubation Time/Temp: | 2 hours at 25° C. |
| Incubation Buffer: | 50 nM Hepes, pH 7.4, 5 mM $MgCl_2$ 1 mM $CaCl_2$, 0.5% BSA |
| NonSpecific Ligand: | 1 µM Somatostatin-14 |
| $K_d$: | 0.79 nM* |
| $B_{max}$: | 1.1 pmol/mg Protein* |
| Specific Binding | 78%* |
| Quantitation Method: | Radioligand Binding |
| Significance Criteria: | ≧50% of max stimulation or inhibition |

*historical values

The protocol for sst4 assay was adapted from Patel, Y. C. and Srikant, C. B. (1994) "Subtype selectivity of peptide analogs for all five cloned human somatostatin receptors (hsstr 1–5)." *Endocrinology* 135 (6): 2814–2817, 1994. The protocol were and can be conducted according to the following conditions.

| Somatostatin sst4 | |
|---|---|
| Source: | Human recombinant CHO-K1 |
| Ligand: | 0.1 nM $^{125}$I Somatostatin-14 |
| Vehicle: | 0.4% DMSO |
| Incubation Time/Temp: | 2 hours at 25° C. |
| Incubation Buffer: | 50 nM Hepes, pH 7.4, 5 mM $MgCl_2$ 1 mM $CaCl_2$, 0.5% BSA |
| NonSpecific Ligand: | 1 µM Somatostatin-14 |
| $K_d$: | 0.87 nM* |
| $B_{max}$: | 0.5 pmol/mg Protein* |
| Specific Binding | 60%* |
| Quantitation Method: | Radioligand Binding |
| Significance Criteria: | ≧50% of max stimulation or inhibition |

*historical values

Compounds of the present invention were assessed for activity in tissue assays directed to sst2 receptors. The assays were conducted by MDS Pharma Services—Taiwan Ltd., Pharmacology Laboratories, 158 Li-The Road, Peitou, Taipei, Taiwan 112, R.O.C.

The protocol for sst2 tissue assay was adapted from Feniuk, W., Dimech, J., and Humphrey, P. P. A. (1993) "Characterization of somatostatin receptors in guinea pig isolated ileum, vas deferens and right atrium. *Br. J. Pharmacol.* 110:1156–1164. The protocol were and can be conducted according to the following conditions.

| Somatostatin sst2 | |
|---|---|
| Source: | Duncan Hartley Guinea pig 325 ± 25 g ileum |
| Vehicle: | 0.1% DMSO |
| Incubation Time/Temp: | 5 minutes at 32° C. |
| Incubation Buffer: | Krebs, pH 7.4 |
| Administration volume: | 10 µL |
| Bath volume: | 10 µL |
| Time of assessment: | 5 minutes |
| Quantitation Method: | Isometric (gram changes) |
| Significance Criteria - Agonist: | ≧50% Inhibition of contraction relative to somatostatin$_{28}$ responses |
| Significance Criteria - Antagonist: | ≧50% Inhibition of somatostatin$_{28}$ relaxant response |

Statistical Methods

The statistical and analytical methods used in this example were adapted from the scientific literature to maximize reliability and reproducibility of the results. Reference standards were run as an integral part of each assay to ensure the validity of the results obtained. Assays were performed under conditions described in the following methods section.

$IC_{50}$ values were determined by a non-linear, least squares regression analysis using Data Analysis Toolbox™ (MDL Information Systems, San Leandro, Calif., USA). Where inhibition constants ($K_i$) are presented, the $K_i$ values were calculated using the equation of Cheng and Prusoff (Cheng, Y., Prusoff, W. H., Biochem. Pharmacol. 22:3099–3108, 1973) using the observed $IC_{50}$ of the tested compound, the concentration of the radioligand employed in the assay, and the historical values for the $K_d$ of the ligand (obtained experimentally at MDS Pharma Services). Where presented, the Hill coefficient ($n_H$), defining the slope of the competitive binding curve, was calculated using Data Analysis Toolbox™. Hill coefficients significantly different than 1.0, may suggest that the binding displacement does not follow the laws of mass action with a single binding site. Where $IC_{50}$, $K_i$ and/or $n_H$ data are presented without Standard Error of the Mean (SEM), data are insufficient to be quantitative, and the values presented ($K_i$, $IC_{50}$, $n_H$) should be interpreted accordingly.

Administration

The compounds of the present invention are administered at a therapeutically effective dosage, i.e., that amount which, when administered to a mammal in need thereof, is sufficient to effect treatment, as described above. Administration of the active compounds and salts described herein can be by any of the accepted modes of administration for agents that serve similar utilities.

The level of the drug in a formulation can vary within the full range employed by those skilled in the art, for example, from about 0.01 percent weight (% w) to about 99.99% w of the drug based on the total formulation and about 0.01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art.

Administration can be by any accepted systemic or local route, for example, by parenteral, oral (particularly for infant formulations), intravenous, nasal, transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington: The Science and Practice of Pharmacy," (formerly called Remington's Pharmaceutical Sciences), edited by Alfonso R. Gennaro, Mack Publishing Company Easton Pa. 18042.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of the present invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the total formulation and about b 0.01% w to 99.99% w excipient. Preferably, the formulation will be about 3.5 to 60% by weight of the pharmaceutically active compound, with the remainder being suitable pharmaceutical excipients.

Intravenous Administration

Intravenous injection has proven to be an important route of administration for therapeutic agents. The compounds and compositions of the present present invention can be administered by this route, for example, by dissolving the compound, salt, ester or ether in a suitable solvent (such as water or saline) or incorporation in a liposomal formulation followed, by dispersal into an acceptable infusion fluid. A typical daily dose of a compound or composition of the invention can be administered by one infusion, or by a series of infusions spaced over periodic intervals.

Oral Administration

Oral administration can be used to deliver the compound of Formula I using a convenient daily dosage regimen that can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill, or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinyl-pyrrolidone, gum acacia, gelatin, cellulose and derivatives thereof, and the like. For oral administration to infants, a liquid formulation (such as a syrup or suspension) is preferred.

Liposomal Formations

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., J. Infect. Dis., 151: 704–710 (1985); Gotfredsen et al., Biochemical Pharmacology, 32: 3389–3396 (1983)]; or to the reticuloendothelial system [see Eppstein et al., Int. J. Immunotherapy, 2:115–126 (1986)], to increase duration of drug action [see: Gabizon et al., Cancer Res., 42: 4734 (1982); Eppstein et al., Delivery Systems for Peptide Drugs, Eds. S. S. Davis, L. Illum and E. Tomlinson, Plenum Pub. Corp., New York, pp. 277–283; C. A. Hunt, Biochemica et Biophysica Acta., 719: 450–463 (1982); and Senior et al., Biochemica et Biophysica Acta., 839: 1–8 (1985)], or to divert a drug away from organs that are particularly sensitive to its toxic effects [see: Weinstein et al., Pharmac. Ther., 24: 207–233 (1983); Olson et al., Eur. J. Cancer Clin. Oncol., 18: 167–176 (1982); and Gabzion et al. supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intesting capsules have also been suggested, see U.S. Pat. No. 4,348,384. The foregoing are incorporated herein by reference.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from 1 wt/wt % to about 2 wt/wt %.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for examle, water, saline, aqueous dextrose, glycerol, ethanol and the like, to thereby form a solution or suspension.

Actual methods of preparing such dosage forms are known, or will be apparent, to those skilled in this art; for example, see "Remington: The Science and Practice of Pharmacy," (formerly called Remington's Pharmaceutical Sciences), edited by Alfonso R. Gennaro, Mack Publishing Company Easton Pa. 18042. The composition to be administered will, in any event, contain a quantity of the active compound(s) in a pharmaceutically effective amount for relief of the particular condition being treated in accordance with the teachings of this invention.

References are cited throughout the specification. These references in their entirety are incorporated by reference into the specification to more fully describe the state of the art to which it pertains.

The following examples are intended to illustrate but not limit the present invention.

EXAMPLES

Example 1

Preparation of 4-Phenoxyaniline-3'-bromopropionamide

1A: Preparation of Compound 1, where $R^1$ is phenyl.

A well stirred solution of 3-phenoxyaniline (1.85 g, 10 mmol) in 20 mL of dichloromethane (DCM) was treated successively with 3-bromopropionic acid (1.74 g, 11 mmol), 1-(3-dimethylaminopropyl)-3-ethylcarbodiimide HCl (EDC) (2.35 g, 12 mmol) and 4-dimethylaminopyridine (0.06 g, 0.5 mmol), under an atmosphere of dry nitrogen. The resulting solution was allowed to stir for 30 min. at room temperature. The mixture was then poured into 150 mL of chloroform and washed successively with 50 mL 1 N HCl, 50 mL water, sat. aqueous $NaHCO_3$ (2×50 mL), 50 mL brine then dried ($Na_2SO_4$) and evaporated. This oil (2.4 g, 100% crude yield) was used directly in the next steps.

Example 2

Preparation of 4-Benzyloxyaniline-3'-bromopropionamide

2A: Preparation of Compound 1, where $R^1$ is benzyl.

A well stirred solution of 3-benzyloxyaniline (5.08 g, 25 mmol) in 40 mL of DCM was treated successively with 3-bromopropionic acid (4.34 g, 27.5 mmol), 1-(3-dimethylaminopropyl)-3-ethyl-carbodiimide HCl (EDC) (5.61 g, 28.7 mmol) and 4-dimethylaminopyridine (0.305 g, 2.5 mmol), under an atmosphere of dry nitrogen. The resulting solution was allowed to stir for 30 min. at room temperature. The mixture was then poured into 150 mL of chloroform and washed successively with 50 mL 1 N HCl, 50 mL water, sat. aqueous $NaHCO_3$ (2×50 mL), 50 mL brine then dried ($Na_2SO_4$), filtered though a pad of silica gel and the filtrate evaporated. This oil (8 g, 96% yield) was used directly in the next steps. $^1H$ NMR ($CDCl_3$) δ 2.93 (t, 2H), 3.71 (t, 2H), 5.07 (s, 2H), 6.7–7.5 (m, 9H).

Example 3

Preparation of 1-(3-Benzyloxy-phenyl)-azetidin-2-one

3A: Compound 2, where $R^1$ is benzyl.

A well stirred solution of Compound 1 (where $R^1$ is benzyl) prepared as above and used directly (8.35 g, 25 mmol) in 150 mL of DCM was treated successively with KOH (1.4 g, 25 mmol), and tetrabutylammonium bromide (8.06 g, 25 mmol) under an atmosphere of dry nitrogen. The resulting solution was allowed to stir for 3 h at room temperature. The mixture was then poured into 150 mL of DCM and washed successively 50 mL water, sat. aqueous $NH_4Cl$ (2×50 mL) and 50 mL brine then dried ($Na_2SO_4$) and evaporated. This residue was then purified by column chromatography (methanol/DCM 1/300) to give 4.5 g (74%) of pure material. M.p.=96–98° C. $^1H$ NMR ($CDCl_3$) δ 2.93 (t, 2H), 3.71 (t, 2H), 5.07 (s, 2H), 6.7–7.5 (m, 9H). Cald. for $C_{16}H_{15}NO_2$: C, 75.87%, N, 5.53%, H, 5.97%; Found: C, 75.60%, H, 5.97%, N, 5.48%.

Example 4

Preparation of 1-(3-Phenyloxy-phenyl)-azetidin-2-one

4A: Preparation of Compound 2, where $R^1$ is phenyl.

A well-stirred solution of Compound 1, where $R^1$ is phenyl, (3.2 g, 10 mmol) in 100 mL of DCM was treated successively with KOH (0.589 g, 10.5 mmol), and 18-crown-6 (2.77 g, 10.5 mmol) under an atmosphere of dry nitrogen. The resulting solution was allowed to stir for 3 h at room temperature. The mixture was then poured into 150 mL of DCM and washed successively 50 mL water, sat. aqueous $NH_4Cl$ (2×50 mL) and 50 mL brine then dried ($Na_2SO_4$) and evaporated. This residue was then purified by column chromatography (methanol/DCM 1/200) to give 2.3 g (100%) of pure material. $^1H$ NMR ($CDCl_3$) δ 3.10 (t, 2H), 3.60 (t, 2H), 6.7–7.5 (m, 9H). M.p.=102–103° C. Cald. for $C_{23}H_{19}NO_4$: C, 73.98%, H, 5.13%, N, 3.75%; Found C, 74.02%, H, 5.29%, N, 3.74%.

Example 5

Preparation of 7-Benzyloxy-2,3-dihydro-1H-quinolin-4-one

5A: Preparation of Compound 3, where $R^1$ is benzyl.

A well-stirred solution of Compound 2, where $R^1$ is benzyl, prepared as above, (10 g, 39.5 mmol) in 300 mL of dichloroethane was treated with polyphosphoric ester (PPE) (100 g,) under an atmosphere of dry nitrogen. The resulting solution was allowed to stir then heated to reflux for 1.5 h. The mixture was then evaporated to approximately 100 mL and poured into 500 mL of ice/water. This was extracted with ethyl acetate (3×150 mL), these combined extracts were washed with 150 mL water, sat. aqueous $NaHCO_3$ (2×50 mL) and 50 mL brine, then dried ($Na_2SO_4$) and evaporated. This residue was then purified by column chromatography (methanol/DCM 1/300, then hexane/ethyl acetate with 2% isopropanol) to give 3 g (30% yield) of pure material. $^1$H NMR ($CDCl_3$) δ 2.66 (t, 2H), 3.55 (t, 2H), 4.33 (bs, 1H), 6.10 (d, 1H), 6.37 (dd, 1H), 7.06 (d, 2H), 7.19 (t, 1H), 7.38 (t, 2H), 7.82 (d, 1H).

Example 6

Preparation of 7-Phenoxy-2,3-dihydro-1H-quinolin-4-one

6A: Preparation of Compound 3, where $R^1$ is phenyl.

A well-stirred solution of Compound 2, where $R^1$ is phenyl, (2.3 g, 9.6 mmol) in 30 mL of trifluoroacetic acid (TFA) was refluxed for 1 h under an atmosphere of dry nitrogen. The resulting solution was diluted with ice/water, treated with 35 mL of 28% aqueous $NH_3$ and extracted with chloroform (2×100 mL). The combined extracts were dried ($Na_2SO_4$) and evaporated. This residue was then purified by column chromatography (methanol/DCM 1/4) to give 0.85 g (36% yield) of 7-phenoxy-2,3-dihydro-1H-quinolin-4-one; $^1$H NMR ($CDCl_3$) δ 2.66 (t, 2H), 3.55 (t, 2H), 4.33 (bs, 1H), 6.10 (d, 1H), 6.37 (dd, 1H), 7.06 (d, 2H), 7.19 (t, 1H), 7.38 (t, 2H), 7.82 (d, 1H). A related by-product 5-phenoxy-2,3-dihydro-1H-quinolin-4-one was also isolated and characterized (0.44 g, 18%); $^1$H NMR ($CDCl_3$) δ 2.68 (t, 2H), 4.20 (t, 2H), 4.50 (bs, 1H), 6.13 (d, 1H), 6.39 (d, 1H), 7.00 (d, 2H), 7.08 (t, 1H), 7.13 (t, 2H), 7.31 (t, 1H).

Example 7

Preparation of 1-Benzyloxycarbonyl-7-benzyloxy-4-3,4-dihydro-2H-quinoline

7A: Preparation of Compound 4, where $R^1$ and $R^2$ are benzyl.

A well-stirred solution of Compound 3, where $R^1$ is benzyl, (2 g, 7.89 mmol) in 30 mL of DCM containing diisopropylethylamine (4.1 g, 31.56 mmol) was treated drop wise with benzyl chloroformate (4.0 g, 23.68 mmol) under an atmosphere of dry nitrogen. The resulting mixture was allowed to stir for 48 h then diluted with 20 mL of DCM. This mixture was then washed with 100 mL of water, 150 mL of 1 N HCl, and sat. aqueous $NaHCO_3$ (2×50 mL), then dried ($Na_2SO_4$) and evaporated. This residue was then purified by column chromatography (hexane/ethyl acetate 5/1 to 4/1) to give 3.0 9 (98% yield) of pure material. $^1$H NMR ($CDCl_3$) δ 2.72 (t, 2H), 4.22 (t, 2H), 4.99 (s, 2H), 5.28 (s, 2H), 6.78 (dd, 1H), 7.3–7.5 (m, 11H), 7.95 (d, 1H).

7B: Preparation of Compound 4, where $R^1$ is phenyl, and $R^2$ is benzyl.

Using the above procedure in Example 7A, and substituting for Compound 3, where $R^1$ is benzyl, with a Compound 3, where $R^1$ is phenyl, gave the desired compound, 1-benzyloxycarbonyl-7-phenyloxy-4-oxo-3,4-dihydro-2H-quinoline. $^1$H NMR (CDCl3) δ 2.74 (t, 2H), 4.21 (t, 2H), 4.99 (s, 2H), 5.22 (s, 2H), 6.76 (dd, 1H), 7.06 (d, 2H), 7.22 (t, 1H), 7.3–7.4 (m, 7H), 7.97 (d, 1H).

Example 8

Preparation of 7-Phenoxy-3,4-dihydro-2H-quinoline-1-carboxylic acid benzyl ester-4-spiro-5'-imidazolidine-2',4'-dione 8A: Preparation of Compound 5, where $R^1$ is phenyl, and $R^{2A}$ is benzyl.

A well-stirred solution of Compound 4, where $R^1$ is phenyl, and $R^{2A}$ is benzyl, (0.3 g, 0.80 mmol) in 5 mL of 95% ethanol containing 5% water, was treated with ammonium carbonate (1.42 g, 14.77 mmol) and KCN (208 mg, 3.19 mmol). This was heated in a sealed pressure tube for 72 h then poured into dilute aqueous HCl and extracted with ethyl acetate (3×150 mL), these combined extracts were dried ($Na_2SO_4$) and evaporated. This residue was then purified by column chromatography ($CHCl_3$/methanol 60/1 to 50/1) to give 250 mg (70% yield) of pure 7-phenoxy-3,4-dihydro-2H-quinoline-1-carboxylic acid benzyl ester-4-spiro-5'-imidazolidine-2',4'-dione. 50 mg of starting material, Compound 4, was also recovered from the column. $^1$H NMR ($CDCl_3$) δ 2.14 (m, 1H), 2.36 (m, 1H), 3.95 (m, 1H), 4.21 (m, 1H), 5.18 (s, 2H), 6.24 (s, 1H), 6.72 (dd, 1H), 6.99 (d, 2H), 7.09 (d, 1H), 7.12 (t, 1H), 7.3–7.4 (m, 7H), 7.52 (bs, 1H), 8.41 (bs, 1H). MS parent $[M+Na]^+$=466.7 amu (observed): $[M+Na]^+$=466.1 amu (theoretical).

Example 9

Preparation of 7-Benzyloxy-3,4-dihydro-2H-quinoline-1-carboxylic acid benzyl ester-4-spiro-5'-imidazolidine-2',4'-dione 9A: Preparation of Compound 5, where $R^1$ is benzyl, and $R^{2A}$ is benzyl.

A well-stirred solution of Compound 4, where $R^1$ is benzyl, and $R^{2A}$ is benzyl, (1 g, 2.58 mmol) in 20 mL of absolute ethanol was treated with ammonium carbonate (2.48 g, 25.8 mmol) and KCN (670 mg, 10.32 mmol). This was heated in a sealed pressure tube for 72 h then poured into dilute aqueous HCl and extracted with ethyl acetate (3×150 mL), these combined extracts were dried ($NaSO_4$) and evaporated. This residue was then purified by column chromatography ($CHCl_3$/methanol 100/1 to 60/1) gave 1 g (85% yield) of pure title compound. $^1$H NMR ($CDCl_3$) δ 2.12 (m, 1H), 2.35 (m, 1H), 3.94 (m, 1H), 4.21 (m, 1H), 4.89 (s, 2H), 5.23 (s, 2H), 6.09 (s, 1H), 6.71 (dd, 1H), 7.04 (d, 1H), 7.12 (t, 1H), 7.3–7.4 (m, 9H), 7.51 (bs, 1H), 8.26 (bs, 1H). MS parent $[M+Na]^+$=480.5 amu (theoretical).

Example 10

Preparation of 7-Benzyloxy-3,4-dihydro-2H-quinoline-1-carboxylic acid benzyl ester-4-spiro-5'-3'-optionally substituted-imidazolidine-2',4'-dione 10A: Preparation of Compound 6, where $R^1$, $R^{2A}$, and $R^3$ are benzyl.

A well-stirred solution of Compound 5, where $R^1$ is benzyl, and $R^{2A}$ is benzyl, (46 mg, 0.1 mmol) in 3 mL of anhydrous dimethylformamide (DMF) was treated with cesium bicarbonate (38 mg, 0.2 mmol) and benzyl bromide (25 mg, 0.15 mmol). This was allowed to stir under nitrogen and heated to 60° C. for 12 h. The mixture was allowed to cool to room temperature then poured into saturated aqueous $NH_4Cl$ and extracted with ethyl acetate (3×25 mL), these combined extracts were washed with water then brine, dried (Na$_2$SO$_4$) and evaporated. This residue crystallized to give a white solid 50 mg (91% yield) of pure title compound, 7-Benzyloxy-3,4-dihydro-2H-quinoline-1-carboxylic acid benzyl ester-4-spiro-5'-3'-benzyl-imidazolidine-2',4'-dione, as a 2:1 complex with DMF. M.p.=171–174° C. $^1$H NMR (CDCl$_3$) δ 2.09 (m, 1H), 2.30 (m, 1H), 2.92 (d, 3H [DMF]), 3.98 (m, 1H), 4.25 (m, 1H), 4.70 (q, 2H), 4.89 (s, 2H), 5.24 (s, 2H), 5.60 (s, 1H), 6.63 (dd, 1H), 6.80 (d, 1H), 7.3–7.4 (m, 15H), 7.51 (bs, 1H), 8.01 (s, 0.5H [DMF]) MS parent [M+Na]$^+$=570.8 amu (observed). Cald. for C$_{33}$H$_{29}$N$_3$O$_5$. 0.5 C$_3$H$_7$NO; C, 70.94%, H, 5.61%, N, 8.39%; Found: C, 70.41%, H, 5.69%, N, 8.40%.

10B: Preparation of Compound 6, where R$^1$, and R$^{2A}$ are benzyl, and R$^3$ is 2-methylprop-1-yl.

Using the procedure Example 11A above, Compound 5, where R$^1$ and R$^{2A}$ are benzyl, (175 mg, 0.383 mmol) gave the desired product, 7-Benzyloxy-3,4-dihydro-2H-quinoline-1-carboxylic acid benzyl ester-4-spiro-5'-3'-(2-methyl-prop-1-yl)-imidazolidine-2',4'-dione, as a white solid 230 mg (93% yield) M.p.=216–219° C. $^1$H NMR (CDCl$_3$) δ 0.9 (m, 6H), 2.10 (m, 2H), 2.32 (m, 1H), 3.37 (d, 2H), 4.00 (m, 1H), 4.26 (m, 1H), 4.91 (s, 2H), 5.24 (q, 2H), 5.54 (s, 1H), 6.72 (dd, 1H), 6.98 (d, 1H), 7.3–7.4 (m, 10H), 7.53 (bs, 1H), MS parent [M+Na]$^+$=536.5 amu (observed).

10C: Preparation of Compound 6, where R$^1$, and R$^{2A}$ are benzyl, and R$^3$=3-methyl-indole-1-carboxylic acid tert-butyl ester.

Using the procedure describe above (at room temperature for 48 h) Compound 5, where R$^1$ and R$^{2A}$ are benzyl, (246 mg, 0.538 mmol) is treated with the alkylating agent, 3-methanesulfonyl-oxymethyl-indole-1-carboxylic acid tert-butyl ester [as prepared in Example 12] to obtained the desired product, 7-Benzyloxy-3,4-dihydro-2H-quinoline-1-carboxylic acid benzyl ester-4-spiro-5'-3'-(3-methyl-1H-indole-1-carboxylic acid tert-butyl ester)-imidazolidine-2',4'-dione, as an oil, 240 mg (76% yield). $^1$H NMR (CDCl$_3$) δ 1.66 (s, 9H), 2.05 (m, 2H), 2.29 (m, 1H), 3.93 (m, 1H), 4.24 (m, 1H), 4.86 (m, 4H), 5.59 (s, 1H), 6.50 (dd, 1H), 6.71 (d, 1H), 7.1–7.5 (m, 15H), 7.69 (s, 1H), 7.72 (s, 1H), 8.13 (bd, 1H). MS parent [M+Na]$^+$=709.7 amu (observed).

10D: Preparation of Compound 6, where R$^1$ is phenyl, R$^{2A}$ is benzyl, and R$^3$ is 3-methyl-indole-1-carboxylic acid tert-butyl ester.

Using the procedure describe above (at room temperature for 48 h) Compound 5, R$^1$ is phenyl, and R$^{2A}$ is benzyl, (208 mg, 0.469 mmol) is treated with the alkylating agent, 3-methanesulfonyloxymethyl-indole-1-carboxylic acid tert-butyl ester [as prepared in Example 12] to obtained the desired product, 7-phenoxy-3,4-dihydro-2H-quinoline-1-carboxylic acid benzyl ester-4-spiro-5'-3'-(3-Methyl-1H-indole-1-carboxylic acid tert-butyl ester)-imidazolidine-2',4'-dione, as an oil, 280 mg (76% yield). $^1$H NMR (CDCl$_3$) δ 1.65 (s, 9H), 2.07 (m, 2H), 2.31 (m, 1H), 3.94 (m, 1H), 4.24 (m, 1H), 4.83 (m, 2H), 5.20 (s, 2H), 5.69 (s, 1H), 6.50 (dd, 1H), 6.73 (d, 1H), 6.9–7.5 (m, 16H), 7.49 (s, 1H), 7.72 (m, 2H), 8.13 (bd, 1H). MS parent [M+Na]$^+$=695.9 amu (observed).

10E: Preparation of Compound 6, where R$^1$ is phenyl, R$^{2A}$ is benzyl, and R$^3$ is 4-tert-butoxycarbonylaminobut-1-yl).

Using the procedure described in Example 10A for the preparation of Compound 6, (where R$^1$ and R$^{2A}$ are benzyl, and R$^3$ is 2-methyl-prop-1-yl), Compound 5 (where R$^1$ is phenyl, R$^2$ is benzyl, 266 mg, 0.6 mmol) is treated with 4-butoxy-carbonylamino-1-methansulfonate (240 mg, 0.9 mmol, prepared according to the procedure of Mattingly, P. Synthesis, 1990, 366–368), which acts as an alkylating agent. The procedure provided the desired product, 7-Benzyloxy-3,4-dihydro-2H-quinoline -1-carboxylic acid benzyl ester-4-spiro-5'-3'-(4-tert-butoxycarbonylaminobut-1-yl)-imidazolidine-2',4'-dione, as an oil, 250 mg (68% yield). $^1$H NMR (CDCl$_3$) δ 1.41 (s, 9H), 1.52 (m, 4H), 1.68 (m, 2H), 2.12 (m, 1H), 2.32 (m, 1H), 2.91 (d, 3H) [0.5 DMF], 3.13 (m, 2H), 3.56 (m, 2H), 3.98 (m, 1H), 4.26 (m, 1H), 4.58 (bs, 1H), 4.86 (m, 4H), 5.18 (s, 2H), 5.88 (s, 1H), 6.73 (dd, 1H), 6.90–7.01 (m, 3H), 7.1–7.5 (m, 9H), 7.53 (bs, 1H), 8.00 (s, 0.5H) [0.5 DMF], MS parent [M+Na]$^+$=637.8 amu (observed).

10F: Preparation of Compound 6, where R$^1$, and R$^{2A}$ are benzyl, and R$^3$ is 4-tert-butoxycarbonylaminobut-1-yl.

Using the procedure described in Example 10A for Compound 6 (where R$^1$, and R$^{2A}$ are benzyl, R$^3$ is 4-tert-butoxycarbonylaminobut-1-yl), Compound 5 (where R$^1$, and R$^{2A}$ are benzyl, 532 mg, 1.2 mmol) is treated with the alkylating agent, 4-butoxycarbonylamino-1-methansulfonate (480 mg, 1.8 mmol), prepared according to the procedure of Mattingly, P. Synthesis, 1990, 366–368) and cesium bicarbonate (460 mg, 2.36 mmol), to provide the desired compound, 7-Benzyloxy-3,4-dihydro-2H-quinoline-1-carboxylic acid benzyl ester-4-spiro-5'-3'-(4-tert-butoxycarbonyl-aminobut-1-yl)-imidazolidine-2',4'-dione as an oil, 370 mg (100% yield). $^1$H NMR (CDCl3) 1.41 (s, 9H), 1.52 (m, 4H), 1.68 (m, 2H), 2.07 (m, 1H), 2.29 (m, 1H), 3.14 (m, 2H), 3.56 (m, 2H), 3.98 (m, 1H), 4.26 (m, 1H), 4.58 (bs, 1H), 4.90 (s, 2H), 5.24 (s, 2H), 5.78 (bs, 1H), 6.71 (dd, 1H), 6.92 (d, 1H), 7.1–7.4 (m, 8H), 7.52 (bs, 1H). MS parent [M+Na]$^+$=651.7 amu (observed).

Example 11

Preparation of 7-Benzyloxy-3,4-dihydro-2H-quinoline-1-carboxylic acidbenzyl ester-4-spiro-5'-3'-benzyl-1'-methyl-imidazolidine-2',4'-dione 11A: Preparation of Compound 7, where R$^1$, R$^{2A}$, and R$^3$ are benzyl, and R$^4$ is CH$_3$ A well-stirred solution of Compound 6, where R$^1$, R$^{2A}$, and R$^3$ are benzyl, and R$^4$=H, (250 mg, 0.456 mmol) in 7 mL of anhydrous DMF was treated with K$_2$CO$_3$ (126 mg, 0.912 mmol) and iodomethane (25 mg, 0.15 mmol). The solution was allowed to stir in a sealed vessel for 18 h. The mixture was poured into saturated aqueous NH$_4$Cl and extracted with ethyl acetate (3×25 mL), these combined extracts were washed with water then brine, dried (Na$_2$SO$_4$) and evaporated. This residue was purified by chromatography (hexane:ethyl acetate 5:1) to give 218 mg (85% yield) of pure 7-benzyloxy-3,4-dihydro-2H-quinoline-1-carboxylic acid benzyl ester-4-spiro-5'-3'-benzyl-1'-methyl-imidazolidine-2',4'-dione. $^1$H NMR CDCl$_3$) δ 2.12 (m, 2H), 4.18 (m, 1H), 4.26 (m, 1H), 4.90 s, 2H), 5.26 (q, 2H), 6.63 (s, 2H), 7.3–7.4 (m, 15H) 7.53 (bs, 1H), MS parent [M+Na]$^+$=584.6 amu (observed).

Example 12

Preparation of 7-Benzyloxy-3,4-dihydro-2H-quinoline-1-carboxylic acid benzyl ester-4-spiro-5'-3'-(2-methylprop-1-yl)-1'-methyl-imidazolidine-2',4'-dione 12A: Preparation of Compound 7, where R$^1$ and R$^{2A}$ are benzyl, R$^3$ is 2-methylprop-1-yl, and R$^4$ is methyl.

A well-stirred solution of Compound 6, where R$^1$, and R$^{2A}$ are benzyl, R$^3$ is methyl, and R$^4$ is H (0.220 g, 0.428 mmol) and 0.118 g (0.856 mmol) of K$_2$CO$_3$ in 7 mL of anhydrous DMF in a capped vial was added 80 μL (1.284 mmol) of iodomethane at room temperature then worked up as above. The product was purified by a filtration through a silica plug, washing with $CHCl_3$ to afford 0.225 g of 7-benzyloxy-3,4-dihydro-2H-quinoline-1-carboxylic acid benzyl ester-4-spiro-5'-1'-methyl-3'-(2-methylprop-1-yl)-imidazolidine-2',4'-dione as a colorless oil (99% yield). $^1$H NMR $(CDCl_3)$ δ(7.55 (bs, 1H), 7.42 (m, 10H), 6.79 (d, 1H), 6.70 (m, 1H), 5.26 (m, 2H), 4.91 (s, 2H), 4.26 (m, 2H), 3.34 (d, 2H), 2.71 (s, 3H), 2.13 (m, 3H), 0.8 (t, 6H). MS parent $[M+H]^+=528$, $[M+Na]^+=550$ amu (observed).

12B: Preparation of Compound 7, where $R^1$ is phenyl, $R^{2A}$ is benzyl, $R^3$ is 3-methyl-indole-1-carboxylic acid tert-butyl ester, and $R^4$ is $CH_3$.

Using the above procedure Compound 6, where $R^1$ is phenyl, $R^{2A}$ is benzyl, $R^3$ is 3-methyl-indole-1-carboxylic acid tert-butyl ester) was converted to the 7-phenoxy-3,4-dihydro-2H-quinoline-1-carboxylic acid benzyl ester-4-spiro-5'-3'-(3-methyl-indole-1-carboxylic acid tert-butyl ester)-1'-methyl-imidazolidine-2',4'-dione (as a colorless oil) in near quantitative yield as a 0.5 DMF complex. $^1$H NMR $(CDCl_3)$ δ[the DMF peaks are not reported] 1.65 (s, 9H), 2.11 (m, 2H), 2.70 (m, 4H), 4.20 (m, 1H), 4.20 (m, 1H), 4.83 (m, 2H), 5.19 (s, 2H), 6.50 (dd, 1H), 6.61 (d, 1H), 6.9–7.4 (m, 15H), 7.51 (s, 1H), 7.69 (m, 2H). MS parent $[M+Na]^+=709.8$ amu (observed).

Example 13

Preparation of 7-Benzyloxy-3,4-dihydro-2H-quinoline-4-spiro-5'-1'-methyl-3'-(2-methylprop-1-yl)-imidazolidine-2',4'-dione 13A: Preparation of Compound 8, where $R^1$ is H, $R^2$ is H, $R^3$ is 2-methylprop-1-yl, and $R^4$ is $CH_3$ A well-stirred solution of Compound 7, where $R^1$ and $R^2$ are benzyl, $R^3$ is 2-methylprop-1-yl, and $R^4$ is CH3 (0.1 g, 0.189 mmol) and 0.06 g (0.945 mmol) of ammonium formate in 3 mL of MeOH in a capped vial was treated with 0.05 g of solid 10% palladium on charcoal. The mixture was heated at 60° C. for 1 h with stirring, filtered through celite bed and washed with MeOH. The crude product was further purified by a filtration through a silica plug, washing with $CH_2Cl_2$/MeOH (20/1) to afford the 7-hydroxy-3,4-dihydro-2H-quinoline-4-spiro-5'-3'-methyl-1'-(2-methylprop-1-yl)-imidazolidine-2',4'-dione as a colorless oil. $^1$H NMR $(CDCl_3)$ δ 6.57 (d, 1H), 6.11 (m, 1H), 5.99 (d, 1H), 5.43 (bs, 1H); 3.98 (m, 3H), 3.34 (m, 3H), 2.76 (s, 3H), 2.21 (m, 3H), 1.97 (m, 1H), 0.95 (t, 6H).

13B: Preparation of Compound 8, where $R^1$ is phenyl, $R^2$ is H, $R^3$ is 3-methyl-indole-1-carboxylic acid tert-butyl ester, $R^4$ is $CH_3$).

Using the above procedure Compound 7, where $R^1$ phenyl, $R^2$ is benzyl, $R^3$ is 3-methyl-indole-1-carboxylic acid tert-butyl ester, and $R^4$ is $CH_3$) was converted to the 7-phenoxy-3,4-dihydro-2H-quinoline-4-spiro-5'-3'-(3-methyl-indole-1-carboxylic acid tert-butyl ester)-1'-methyl-imidazolidine-2',4'-dione in near quantitative yield as the 0.5 DMF complex. $^1$H NMR $(CDCl_3)$ [the DMF peaks are not reported] δ 1.65 (s, 9H), 2.11 (m, 2H), 2.70 (m, 4H), 4.20 (m, 1H), 4.20 (m, 1H), 4.83 (m, 2H), 5.19 (s, 2H), 6.50 (dd, 1H), 6.61 (d, 1H), 6.9–7.4 (m, 15H), 7.51 (s, 1H), 7.69 (m, 2H). MS parent $[M+Na]^+=709.8$ amu (observed).

Example 14

Preparation of 7-Tolyloxy-3,4-dihydro-2H-quinoline-4-spiro-5'-3'-(2-methyl-1-yl)-1'-methylimidazolidine-2',4'-dione 14A: Preparation of a compound of Formula I, where ($R^1$ is 4-tolyl, $R^2$ is H, $R^3$ is 2-methylprop-1-yl, and $R^4$ is —$CH_3$ A mixture of Compound 8, where $R^1$ and $R^2$ are H, $R^3$ is 2-methylprop-1-yl, and $R^4$ is $CH_3$ (25 mg, 0.0824 mmol), $Cu(OAc)_2$ (30 mg, 0.165 mmol), p-tolyl boronic acid (23 mg, 0.169 mmol) and 30 mg of powdered 4 Å molecular sieves in 2 mL of anhydrous $CH_2Cl_2$ in a capped vial was added of triethylamine (58 mL, 0.410 mmol) in an atmosphere of air ($O_2$ is required for the reaction). The mixture was stirred vigorously at room temperature for 24 h (during which the color was observed changing from blue to green) and filtered through silica bed, washing with $CHCl_3$/MeOH (10/1). The filtrate was evaporated and purified by silica gel chromatography with Hexane/EtOAc (3/1–2/1) to afford 25 mg (77% yield) of pure 7-tolyloxy-3,4-dihydoxy-2H-quinoline-4-spiro-5'-3'(2-methyl-1-yl)-1'-methyl-imidazolidine-2',4'-dione as a colorless oil. $^1$H NMR $(CDCl_3)$ δ 7.14 (m, 2H), 6.93 (m, 2H), 6.68 (m, 1H), 6.26 (m, 1H), 6.14 (bs; 1H), 4.02 (m, 2H), 3.32 (m, 3H), 2.78 (s, 3H), 2.36 (s, 3H), 2.16 (m, 2H), 1.92 (m, 1H), 0.90 (t, 6H). MS parent $[M+Na]^+=416$ amu (observed).

Example 15

Preparation of 7-Tolyloxy-3,4-dihydro-2H-quinoline-1-(3-methyl-indole-3yl-1-carboxylic acid-t-butyl ester)-4-spiro-5'-3'-(2-methylprop-1-yl)-methyl-imidazolidine-2',4'-dione 15A: Preparation of a Compound of Formula I, where $R^1$ is 4-tolyl, $R^2$ is indol-3-ylmethyl, $R^3$ is 2-methylprop-1-yl, and $R^4$ is $CH_3$.

A mixture of 3-formyl-indole-1-carboxylic acid t-butyl ester, Compound 9, where $R^1$ is 4-tolyl, $R^2$ is H, $R^3$ is 2-methylprop-1-yl, and $R^4$ is $CH_3$ (9 mg (0.0609 mmol) and $NaBH(OAc)_3$ (17 mg, 0.0812 mmol) in 1 mL of anhydrous $CH_2Cl_2$ was vigorously stirred for 2 days, during which the the initially cloudy solution turned clear. The mixture was partitioned between 5 mL of EtOAc and 3 mL of saturated-$NH_4Cl$ solution and extracted three times. The combined EtOAc layer was washed with brine, dried over $Na_2SO_4$ and evaporated to dryness under vacuum. The product was purified by a silica gel column with Hexane/EtOAc (4/1–2/1) to afford 15 mg of 7-tolyloxy-3,4-dihydro-2H-quinoline-1-(3-methyl-indole-3-yl-1-carboxylic acid t-butyl ester)-4-spiro-5'-3'-1(2-methylpropy-1-yl)-1' methyl-imidazolidine-2',4'-dione as a light brown oil (71% yield).

Example 16

Preparation of 3-Methanesulfonyloxymethyl-indole-1-carboxylic acid tert-butyl ester A well-stirred solution of 3-hydroxymethyl-indole-1-carboxylic acid tert-butyl ester (10, 450 mg, 1.82 mmol) [as prepared following the procedure of D. J. Oliveira and F. Coelho, Synth. Commun. 30 (12) pg. 2143 (2000)] in 10 mL of dichloromethane was cooled in an ice-bath, then treated successively with triethylamine (TEA) (283 mg, 2.18 mmole) and methanesulfonyl chloride (229 mg, 2.0 mmol). This was allowed to stir under nitrogen for 15 min. diluted with dichloromethane, then washed with saturated $NaHCO_3$, dried $(Na_2SO_4)$ and evaporated. This residue was purified by chromatography to give 0.43 g (73% yield) of the desired compound as an unstable brown solid. $^1$H NMR $(CDCl_3)$ δ 1.67 (s, 12H), 4.79 (s, 2H), 7.28 (t, 1H), 7.36 (t, 1H), 7.67 (m, 2H), 7.51 (bd, 1H).

Example 17

Preparation of Benzyl-(4-hydroxy-butyl)-carbamic acid tert-butyl ester

17A: Preparation of 4-Benzylamin-1-ol.

To a solution of 4-amino-butan-1-ol (5 g, 56 mmol) in anhydrous DCM (30 mL), benzaldehyde (7.14 g, 67 mmol) and $Na_2SO_4$ (15 g) were added. The suspension was stirred at room temperature overnight. The DCM was removed under vacuum and the resulting thick oil was dissolved in anhydrous EtOH. $NaBH_4$ (4.2 g 112 mmol) was added to the solution in a portion wise manner over a 10 min period. The milky suspension was stirred at room temperature for an additional 3 h. The reaction mixture was then diluted with water and extracted with EtOAc (3×80 mL). The combined organic layer was washed with water, brine, and dried over $Na_2SO_4$. The solvent was removed under reduce pressure to afford 4-benzylamin-1-ol in 76% yield. $^1H$ NMR ($CDCl_3$) δ 7.37–7.21 (m, 5H); 3.78 (s, 2H); 3.61–3.56 (m, 2H); 3.35 (bs, 2H); 2.70 (t, J=6Hz, 2H); 1.72–1.60 (m, 4H). ELDS/MS: m/z 180 [M+H]$^+$.

17B: Preparation of Benzyl-(4-hydroxy-butyl)-carbamic acid tert butyl ester.

To a suspension of NaOH (0.31 g, 7.7 mmol); and TBAB (0.018 g, 0.57 mmol); in DCM (10 mL) cooled to 0° C. in an ice-water bath, 4-benzylamin-1-ol (as prepared in Example 17A, 0.51 g, 28 mmol) in dichloromethane (10 mL) was added slowly over 5 min. Subsequently the Boc anhydride (0.7 g, 3.1 mmol) in DCM (5 mL) was also added at a rate to keep the internal temperature at 0° C. The stirring was continued for 30 min at 0° C., then the cold bath was removed and the reaction mixture was stirred for additional 6 h at room temperature. The mixture was diluted with water and extracted with DCM (3×50 mL). The organic layer was washed with water, brine, and dried over $Na_2SO_4$. The crude was purified by chromatography on silica gel using a hexane/ethyl acetate mixture (70:30) as eluent to yield benzyl-(4-hydroxy -butyl)-carbamic acid tert butyl ester in quantitative yields. $^1H$ NMR ($CDCl_3$) δ 7.37–7.21 (m, 5H); 5.30 (s, 2H); 4.43 (bs, 2H); 3.61 (bs, 2H); 1.58–1.45 (m, 13H). ELDS/MS: m/z 278 [M+H]$^+$.

Example 18

Preparation of N-Benzyl-N-(t-butoxycarbonyl)-4-amino-1-iodobutane

To a solution of benzyl-(4-hydroxy-butyl)-carbamic acid tert butyl ester (6.06 g 21.7 mmol) in acetonitrile (25 mL), carbonyldiimidazole (3.52 g 21.7 mmol) and iodomethane (6.8 mL 109 mmole) were added. The reaction mixture became lukewarm and was stirred for an hour at room temperature followed by another 2 h under reflux. The reaction mixture was allowed to cool to room temperature and additional iodomethane (6.8 mL) was added and the reaction was refluxed for an additional hour. The reaction mixture was allowed to cool to room temperature and was diluted with diethyl ether (150 mL) resulting in a white suspension that was washed with of water (100 mL). The organic layer was washed successively with, 1N HCl (50 mL), saturated $NaHCO_3$ (50 mL), 5% $Na_2S_2O_3$ (50 mL), and brine. The organic layer was dried on $Na_2SO_4$ and the resulting yellow oil crude was purified by flash chromatography using a 95:5 mixture of ethyl acetate-petroleum ether as eluent to give N-benzyl-N-(t-butoxycarbonyl)-4-amino-1-iodobutane (4.49 g, 53%) as colorless, viscous oil. $^1H$ NMR ($CDCl_3$) δ 7.24–7.35 (m, 5H); 4.42 (bs, 2H); 3.19 (bs, 4H); 1.76 (bs, 2H); 1.6 (bs, 2H); 1.51 (s, 9H).

Example 19

Preparation of N-Benzyl-N-(t-butoxycarbonyl)-4-amino-1-butanal

A commercially available 2 M solution of oxalyl chloride in DCM solution (13.8 mL of 27.6 mmol), obtained from Aldrich Chemical Co., was diluted with anhydrous dichloromethane (50 mL). The solution was cooled to −78° C., and a solution of dimethyl sulfoxide "DMSO" (4.45 ml 62 mmol) in DCM (10 ml) was added over a 45 min period. After the addition was completed a solution of benzyl-(4-hydroxy-butyl)-carbamic acid tert butyl ester (6.9 g, 25 mmol) in DCM (20 mL) was added was added over a 30 min period resulting in a thick white suspension. The reaction mixture was stirred for an additional 15 min followed by the addition of triethylamine TEA (24 mL) over a 30 min period. The cooling bath was removed and stirring was continued for 1 h. The reaction mixture was quenched with water (200 mL) and the layers were separated. The aqueous layer was extracted with ethyl acetate (3×100 mL). The organic layer was washed with water, brine, and dried over $Na_2SO_4$. The crude yellow oil was purified by chromatography using a 8:2 ethyl acetate-hexane mixture as eluent to afford N-benzyl-N-(t-butoxycarbonyl)-4-amino-1-butanal (4.41 g, 63%) as a colorless, viscous oil. $^1H$ NMR δ 9.74 (s, 1H); 7.24–7.36 (m, 5H); 4.41 (bs, 2H); 3.18 (bs, 2H); 2.42 (bs, 2H); 1.66 (bs, 2H); 1.50 (bs, 9H). ELSD/MS: m/z 278 [M+H]$^+$.

Example 20

N-benzyl-N-(t-butoxycarbonyl)-4-amino-1-butanoic acid

A solution of benzyl-(4-hydroxy-butyl)-carbamic acid tert butyl ester (9.4 g, 33.7 mmol) in anhydrous dimethyl formamide "DMF" (40 mL) was cooled in an ice bath. Pyridinium dichromate (44 g, 117 mmol) was added in 4 portions of with 15 min intervals. The reaction mixture was allowed to stir overnight at room temperature resulting in a viscous black slurry. The slurry was poured into water (400 mL), acidified to pH 1 with concentrated HCl and extracted with ethyl acetate (3×100 mL). The combined organic layers were washed with, 5% $NaHSO_4$ (100 mL), water (4×300 mL). Subsequently, the organic layer was extracted with 1M NaOH (150, 75, and 50 mL). The combined aqueous layers were cooled with an ice bath and the pH was adjusted to 3 with concentrated HCl. The resulting white suspension was extracted three times with ethyl acetate (3×200 mL) and the combined organic layers were dried over $Na_2SO_4$, filtered, and the solvent was evaporated in vacuo to give N-benzyl-N-(t-butoxy-carbonyl)-4-amino-1-butanoic acid (4.0 g, 40%) as viscous oil. $^1H$ NMR ($CDCl_3$): δ 7.23–7.35 (m, 5H); 4.41 (bs, 2H); 3.29 (bs, 1H); 3.19 (bs, 1H); 2.33 (bs, 2H); 1.82 (bs, 2H); 1.46 (bs, 9H).

Example 21

Preparation of 7-Phenoxy-3,4-dihydro-2H-quinoline-1-carboxylic acid benzyl ester-4-spiro-5'-3'-methyl-imidazolidine-2',4'-dione 21A: Preparation of Compound 7, where $R^1$ is phenyl, $R^{2A}$ is benzyl, $R^3$ is methyl and $R^4$ is hydrogen A mixture of 7-Phenoxy-3,4-dihydro-2H-quinoline-1-carboxylic acid benzyl ester-4-spiro-5'-imidazolidine-2',4'-dione, as prepared in Example 9, (0.52 g; 0.6 mmol), MeI (0.15 mL, 2.35 mmol), and CsHCO3 (0.45 g, 1.35 mmol) in 10 mL of anhydrous DMF was stirred at room temperature for 24 h. Thin-layer chromatography showed clean conversion of the starting compound to a single product. The mixture was quenched with $H_2O$ and extracted with EtOAc (3×30 mL). The combined EtOAc layer was washed with water, brine, dried over $Na_2SO_4$, and evaporated to dryness under vacuum. The residue was then purified by chromatography on $SiO_2$ using 7:3 hexanes/ethyl acetate mixtures to yield 7-Phenoxy-3,4-dihydro-2H-quinoline-1-carboxylic acid benzyl ester-4-spiro-5'-3'-methyl-imidazolidine-2',4'-dione (0.53 g, 99%). $^1$H NMR (CDCl3) δ 7.55 (bs, 1H); 7.36–7.30 (m, 9H); 7.15–7.10 (m, 1H); 7.03–6.98 (m, 2H); 6.72 (dd, 1H, J=2.4 and 8.7 Hz); 5.59 (bs, 1H); 5.19 (bs, 2H); 4.32–4.23 (m, 2H); 4.01–3.94 (m, 2H); 3.09 (s, 3H); 2.38–2.33 (m, 2H); 2.16–2.08 (m, 2H). ELSD/MS: m/z 458 [M+H]$^+$.

Example 22

Preparation of 7-Phenoxy-3,4-dihydro-2H-quinoline-1-carboxylic acid benzyl ester-4-spiro-5'-1'-(1H-indol-3-ylmethyl)-3'-methyl-imidazolidine-2', 4'-dione 22A: Preparation of Compound 7, where $R^1$ is phenyl, $R^{2A}$ is benzyl, $R^3$ is methyl and $R^4$ is 1-H-indol-3-ylmethyl To a solution of 7-phenoxy-3,4-dihydro-2H-quinoline-1-carboxylic acid benzyl ester-4-spiro-5'-3'-methyl-imidazolidine-2',4'-dione (0.44 g, 0.96 mmol) in anhydrous DMF and cooled at 0° C., NaH (0.027 g, 1.15 mmol) was added portion wise. The suspension was stirred for 30 min. To this solution, a solutions of trimethyl-(1-triisopropylsilanyl)-1-H-indol-3-ylmethyl)ammonium iodide (0.5 g, 1.06 mmol) in DMF (4 mL), and 1M solution TBAF (1.2 mL, 1.15 mmol) were slowly added simultaneously. After the addition was completed the reaction mixture was allowed to stir at room temperature or 8 h. The mixture was diluted with water and extracted with EtOAc (3×30 mL). The combined EtOAc layer was washed with water, brine, dried over $Na_2SO_4$ and evaporated to dryness under vacuum. The residue was purified by chromatography on silica gel, using 7:3 hexanes/ethyl acetate mixtures as eluent to yield 7-phenoxy-3,4-dihydro-2H-quinoline-1-carboxylic acid benzyl ester-4-spiro-5'-1'-(1H-indol-3-ylmethyl)-3'-methyl-imidazolidine-2',4'-dione (0.35 g, 62% yield). $^1$H NMR (CDCl3) δ 7.59 (d, 1H); 7.42–7.30 (m, 7H); 7.22–6.99 (m, 5H); 6.72 (d, 1H); 6.61 (d, 1H); 6.52 (dd, 1H); 5.20 (q, 2H); 4.93 (d, 1H); 4.23 (d, 1H); 4.12 (dt, 1H); 3.89–3.80 (m, 1H); 3.12 (s, 3H); 1.90–1.76 (m, 2H). ELSD/MS: m/z 587 [M+H]$^+$.

Example 23

Preparation of 7-Phenoxy-3,4-dihydro-2H-quinoline-4-spiro-5'-1'-(1H-indol-3-ylmethyl)-3'-methyl-imidazoline-2',4'-dione 23A: Preparation of Compound 8, where $R^1$ is phenyl, $R^2$ is H, $R^3$ is methyl, and $R^4$ is 1H-indol-3-ylmethyl.

To a solution of 7-phenoxy-3,4-dihydro-2H-quinoline-1-carboxylic acid benzyl ester-4-spiro-5'-1'-(1H-indol-3-ylmethyl)-3'-methyl-imidazolidine-2',4'-dione (0.06 g, 0.1 mmol), ammonium formate (0.04 g, 0.6 mmol) in MeOH (3 ml) solid 10% palladium on charcoal (0.05 g) was added. The mixture was heated at 60° C. for 1 h with stirring and filtered through celite bed and washed with MeOH. The crude product was further purified by a filtration through a silica plug, washing with 20:1 $CH_2Cl_2$/MeOH solution to afford 7-phenoxy-3,4-dihydro-2H-quinoline-4-spiro-5'-1'-(1H-indol-3-ylmethyl)-3'-methyl-imidazolidine-2',4'-dione as thick oil. $^1$H NMR (CDCl$_3$) d 8.05 (bs, 1H); 7.68 (d, 1H); 7.31–7.01 (m, 12H), 6.68 (d, 1H); 6.23–6.19 (m, 2H); 5.03 (dd, 1H); 4.23 (d, 1H); 3.97–3.81 (m 2H); 3.49 (bs, 1H); 3.12 (s, 3H); 2.18–2.10 (m, 1H); 1.78–1.73 (m, 2H).

23B: Preparation of Compound 8. where $R^1$ is phenyl, $R^2$ is H, $R^3$ is 3-methyl-indole-1-carboxylic acid tert-butyl ester, and $R^4$ is methyl.

A well-stirred solution of Compound 7, where $R^1$ is phenyl, $R^{2A}$ is benzyl, $R^3$ is 3-methyl-indole-1-carboxylic acid tert-butyl ester and $R^4$ is methyl, (0.1 g, 0.189 mmol) and ammonium formate (0.06 g 0.945 mmol) in 3 ml of MeOH in a capped vial was treated with 0.05 g of solid 10% palladium on charcoal. The mixture was heated at 60° C. for 1 h with stirring, filtered through celite bed and washed with MeOH. The crude product was further purified by filtration through a silica plug, washing with $CH_2Cl_2$/MeOH (20/1) to afford the 7-phenoxy-3,4-dihydro-2H-quinoline-4-spiro-5'-3'-(1H-indol-2-ylmethyl-1-carboxylic acid tert-butyl ester)-1'-methyl-imidazolidine-2$^1$, 4'-dione as a colorless oil in quantitative yields. $^1$H NMR (CDCl$_3$) δ 8.13–8.02 (m, 2H); 7.76–7.64 (m, 2H); 7.35–6.90 (m, 9H); 6.63–6.60 (m, 1H); 6.17–6.12 (m, 2H); 4.81 (s, 2H); 4.18–3.91 (m, 2H); 3.77 (bs, 1H); 3.33–3.27 (m, 1H); 2.70 (s, 3H); 2.29–1.90 (m, 22H); 1.64 (s, 9H).

Example 24

Preparation of 7-phenoxy-3,4-dihydro-2H-quinoline-1-butyl-benzyl-carbamic acid tert-butyl ester-4-spiro-5'-1'-(1H-indol-3-ylmethyl)-3'-methyl-imidazolidine-2',4'-dione 24A: Preparation of a Compound of Formula I, where $R^1$ is phenyl, $R^2$ is 1-butyl-benzyl-carbamic acid tert butyl ester, $R^3$ is methyl; and $R^4$ is 1H-indol-3-yl methyl.

To a solution of 7-phenoxy-3,4-dihydro-2H-quinoline-4-spiro-5'-1'-(1H-indol-3-ylmethyl)-3'-methyl-imidazoline-2', 4'-dione (0.036 g, 0.08 mmol), N-benzyl-N-(t-butoxycarbonyl)-4-amino-1-butanal (0.033 g, 0.12 mmol) in anhydrous DCM (2 mL), NaBH(OAc)$_3$ was added all in once. The reaction mixture was let to stir at room temperature for 8 h. The reaction mixture was diluted with ethyl acetate and washed with water and a 5% NaHCO$_3$, dried over $Na_2SO_4$, and evaporated to dryness under vacuum brine. The crude was purified by chromatography on silica gel using 6:4 hexanes/ethyl acetate mixtures as eluent to yield 7-phenoxy-3,4-dihydro-2H-quinoline-1-butyl-benzyl-carbamic acid tert-butyl ester-4-spiro-5'-1'-(1H-indol-3-ylmethyl)-3'-methyl-imidazolidine-2',4'-dione (0.03 g, 73.2% yield based on recovered SM). $^1$H NMR (CDCl$_3$) δ 7.67–7.65 (m, 1H); 7.36–7.03 (m, 22H); 6.86 (b.s., 1H); 6.68 (d, 1H), 6.30 (b.s., 1H); 6.14 (dd, 1H); 4.42 (b.s., 2H); 3.63 (bs, 2H); 3.22–3.05 (m, 5H); 1.45 (s, 9H); 1.33–1.23 (m, 2H); 0.88 (t, 2H); ELSD/MS: m/z 714 [M+H]$^+$.

Example 25

Preparation of 7-Phenoxy-3,4-dihydro-2H-quinoline-1-(4-benzylamino-butyl)-4-spiro-5'-1'-(1H-indol-3-ylmethyl)-3'-methyl-imidazolidine-2',4'-dione 25A: Preparation of Compound of Formula I, where $R^1$ is phenyl, $R^2$ is 4-benzylamino-butyl, $R^3$ is methyl, and $R^4$ is 1H-indol-3-ylmethyl.

To a solution of 7-phenoxy-3,4-dihydro-2H-quinoline-1-butyl-benzyl-carbamic acid tert-butyl ester-4-spiro-5'-1'-(1H-indol-3-ylmethyl)-3'-methyl-imidazolidine-2',4'-dione (0.03 g, 0.042 mmol) in anhydrous DCM (5 mL) stirred under at room temperature, trifluoroacetic acid (0.5 mL) was added drop wise. The reaction mixture was stirred at this temperature for 30 min and then it was diluted with 0.1N NaOH and extracted with DCM (3×10 mL). The organic was washed with water, brine, dried over $Na_2SO_4$ and evaporated to dryness under vacuum. The crude was purified over a small silica gel column using 9.6:06:0.1 $CH_2Cl_2$-MeOH-$NH_4$ mixture as eluent to afford 7-phenoxy-3,4-dihydro-2H-quinoline-1-(4-benzylamino-butyl)-4-spiro-5'-1'-(1H-indol-3-ylmethyl)-3'-methyl-imidazoline-2',4'-dione (0.020 g 80%) as thick oil. $^1$H NMR ($CDCl_3$) δ 9.39 (bs, 1H); 7.65 (d, 1H); 7.34–7.28 (m, 7H); 7.20 (d, 1H); 7.15 (dd, 1H); 7.11–7.07 (m, 2H); 7.01 (d, 1H); 6.84 (s, 1H); 6.69 (d, 1H), 6.32 (d, 1H); 6.15 (dd, 1H); 5.14 (d, 1H); 4.13 (d, 1H); 3.8 (s, 3H); 3.76 (dt, 1H); 3.29–3.25 (m, 1H); 3.10 (s, 2H); 3.01–2.96 (m, 1H); 2.80–2.77 (m, 1H); 2.69–2.65 (m, 3H); 1.84 (dt, 1H); 1.56–1.48 (m, 6H). ELSD/MS m/z: 614 $(M+H)^+$.

Example 26

Preparation of 7-Phenoxy-3,4-dihydro-2H-quinoline-1-(4-butylamine)-4-spiro-5'-1'-(1H-indol-3-ylmethyl)-3'-methyl-imidazolidine-2',4'-dione 26A: Preparation of a Compound of Formula I, where $R^1$ is phenyl, $R^2$ is 4-butylamino-1-yl, $R^3$ is methyl, and $R^4$ is 1H-indol-3-ylmethyl.

To a solution of 7-phenoxy-3,4-dihydro-2H-quinoline-1-(4-benzylamino-butyl)-4-spiro-5'-1'-(1H-indol-3-ylmethyl)-3'-methyl-imidazolidine-2',4'-dione (0.15 g 0.022 mmol) ammonium formate (0.02 g, 0.22 mmol) in MeOH (3 mL), solid 10% palladium on charcoal (0.02 g) was added. The mixture was heated at 60° C. for 2 h with stirring. The reaction mixture was filtered through a small celite bed and washed with MeOH. The crude product was further purified by a filtration through a silica plug, washing with 9.5/0.5/0.1 DCM/MeOH/$NH_4$ mixtures. The thick oil residue was treated with a 1 M trifluoracetic methanolic solution to yield 7-phenoxy-3,4-dihydro-2H-quinoline-1-(4-butylamine)-4-spiro-5'-1'-(1H-indol-3-ylmethyl)-3'-methyl-imidazolidine-2',4'-dione triflate salt (0.011 g; 91.6%) still as thick oil. $^1$H NMR ($CDCl_3$) 8.6 (bs, 1H); 7.60 (d, 1H); 7.34–7.28 (m, 10H); 7.11–6.95 (m, 7H); 6.64 (d, 1H); 6.25 (bs, 1H); 6.20–6.0 (m, 1H); 5.14 (d, 1H); 4.21–4.10 (m, 2H); 3.6–3.5 (m, 1H); 3.06 (s, 3H); 2.83–2.80 (m, 4H); 2.59–2.50 (m, 2H); 2.20–1.96 (m, 2H); 1.80–1.57 (m, 6H). ELSD/MS: m/z 524 $[M+H]^+$.

Example 27

Preparation of 7-Phenoxy-3,4-dihydro-2H-quinoline-1-(4-oxo-1-yl-butyl-carbamic acid tert-butyl ester)-4-spiro-5'-1'-methyl-3'-(1H-indol-3-ylmethyl 1-carboxylic acid tert-butyl ester)-imidazolidine-2',4'-dione 27A: Preparation of a Compound of Formula I, where $R^1$ is Ph, $R^2$ is -4-oxo-1-yl-butyl-carbamic acid tert-butyl ester, $R^3$ is 3-methyl-indole-1-carboxylic acid tert-butyl ester, and $R^4$ is $CH_3$.

To a well stirred solution of Compound 8 as prepared in Example 22, (0.09 g, 0.163 mmol) and 4-Boc-aminobutyric acid (0.036 g, 0.179 mmol) in anhydrous $CH_2Cl_2$ (2 mL), 1-(3-dimethylaminopropyl)-3-ethycarbodiimide (0.048 g, 0.245 mmol), disopropylethyl amine (1 eq), dimethyl amino pyridine (catalytic amount) were added. The reaction mixture was stirred at R.T. for 24 h. After this time the mixture was quenched with a saturated solution $NaHCO_3$ (5 mL and extracted with $CH_2Cl_2$ (3×10 mL). The organic layer was washed with water, brine and dried over $Na_2SO_4$. The crude was further purified by chromatography on silica gel using 7:3 hexanes/ethyl acetate mixtures as eluent. 7-Phenoxy-3,4-dihydro-2H-quinoline-1-(4-oxo-1-yl-butyl-carbamic acid tert-butyl ester)-4-spiro-5'-1'-methyl-3'-(1H-indol-3-ylmethyl 1-carboxylic acid tert-butyl ester)-imidazolidine-2',4'-dione (0.01 g, 25% yield based on recovered starting material) was obtained as off white solid. $^1$H NMR ($CDCl_3$) δ 8.12 (d, 1H); 7.74–7.60 (m, 2H); 7.41–7.15 (m, 10H); 7.04–6.85 (m, 2H); 4.86–4.74 (m, 2H); 4.34 (bs, 1H); 3.80–3.77 (m, 1H); 3.15–2.98 (m, 2H); 2.49 (s, 3H); 2.57–2.44 (m, 2H); 2.22 (bs, 1H); 2.15–2.07 (m, 1H); 1.87–1.82 (m, 2H); 1.65 (s, 9H); 1.49 (s, 9H); 1.28–1.17 (m, 2H). ELSD/MS: m/z 737 $[M+H]^+$, 760 $[M+Na]^+$.

Example 28

Preparation of 7-Phenoxy-3,4-dihydro-2H-quinoline-1-(4-amino-1-yl-butan-1-one)-4-spiro-5'-1'-methyl-3'-(1H-indol-3-ylmethyl)-imidazolidine-2',4'-dione 28A: Preparation of a Compound of Formula I, where $R^1$ is Ph, $R^2$ is 4-amino-1-yl-butan-1-one, $R^3$ is 3-methyl-indole-1-carboxylic acid, and $R^4$ is $CH_3$.

To a solution of Compound 8, where $R^1$ is Ph, $R^2$ is 4-oxo-1-yl-butyl-carbamic acid t-butyl ester, $R^3$ is 3-methyl-indole-1-carboxylic acid t-buty ester, and $R^4$ is $CH_3$) (10 mg, 0.0135 mmol) in DCM (1 mL) was treated with trifluoro acetic acid (0.3 mL). The reaction mixture was stirred at R.T. for 20 min. After this time the solvent was removed under vacuum and the resulting residue was dried under high vacuum for 1 h. A light brown powder was collected by filtration and washed with diethyl ether to afford 7-Phenoxy-3,4-dihydro-2H-quinoline-1-(4-amino-1-yl-butan-1-one)-4-spiro-5'-1'-methyl-3$^1$-(1H-indol-3-ylmethyl)-imidazolidine-2',4'-dione (7 mg, 70%) as TFA salt. $^1$H NMR (DMSO) δ 11.02 (s, 1H); 7.57 (d, 1H); 7.42–7.7.39 (m, 2H); 7.35 (d, 1H); 7.29–7.16 (m, 2H); 7.08–7.03 (m, 2H); 6.98–6.95 (m, 1H); 6.76 (d, 1H); 6.11 (dd, 1H); 4.74 (s, 2H); 4.11–4.08 (m, 1H); 3.77 (bs, 1H); 2.75–2.72 (m, 2H); 2.70–2.57 (m, 4H); 2.26–2.24 (m, 1H); 2.17–2.12 (m, 1H); 1.77–1.73 (m, 2H). ELSD/MS: m/z 538 $[M+H]^+$.

Example 29

Preparation of Dimethyl-(1-triisopropylsilanyl)-1-H indol-3-ylmethyl)-amine

Prepared following the procedure described by M. Iwao, O. Motoi: Tetrahedron Lett. 36, 5929, 1995. To a solution of Gramine (2 g, 11 mmol) Aldrich in anhydrous DMF (10 mL) and cooled at 0° C. in an ice-water bath, NaH (0.46 g, 15 mmol) was added portion wise over a 10 min period. The red reaction mixture was then stirred for 30 min. Tri-isopropyl-silyl-chloride (2.9 mL, 13 mmol) in DMF (5 mL) was added drop wise. After the addition was completed, the reaction mixture was stirred for 2 h at room temperature. The mixture was then quenched with water and extracted with EtOAc (3×40 mL). The combined organic layer was washed with water, brine, dried over $Na_2SO_4$ and evaporated to dryness under vacuum. The resulting crude was purified by chromatography on silica gel using a mixture of 90:10 hexane/ethyl acetate mixture as solvent, to yield dimethyl-(1-triisopropyl-silanyl)-1-H indol-3-ylmethyl)-amine (3.3 g, 87.3%). $^1$H NMR ($CDCl_3$) δ 7.67–7.64 (m, 3H); 7.49–7.46 (m, 1H); 7.17 (s, 1H); 7.14–7.11 (m, 2H); 3.65 (s, 2H); 2.28 (s, 6H); 1.7 (sept, 3H); 1.36 (d, 18H). ELSD/MS: m/z 661 $[2M+H]^+$.

Example 30

Trimethyl-(1-triisopropylsilanyl)-1-H-indol-3-ylmethyl)-ammonium iodide

Prepared following the procedure described by M. Iwao, O. Motoi: Tetrahedron Lett. 36, 5929, 1995. To a solution of dimethyl-(1-triisopropyl-silanyl)-1-H indol-3-ylmethyl)-amine (0.812 g, 2.45 mmol) in anhydrous benzene (15 mL), MeI (0.69 g, 4.9 mmol) was added. After the addition was completed, a white solid precipitated out of the solution. The mixture was stirred for 2 h. The solvent was removed under vacuum to yield trimethyl-(1-triisopropylsilanyl)-1H-indol-3-ylmethyl) 1-ammonium iodide (1.1 g, 99%) as white powder.

Example 31

Determination of Biochemical and Radio Ligand Binding

This example teaches representative compounds of the present invention that have binding activity to receptors that are known to be associated with various therapeutic disorders.

Compound A [7-phenoxy-3,4-dihydro-2H-quinoline-1-(4-amino-butanonyl)-4-spiro-5'-1'-methyl-3'-(1H-indol-3-ylmethyl)-imidazolidine-2',4'-dione] and Compound B [7-phenoxy-3,4-dihydro-2H-quinoline-1-(4-butylamine)-4-spiro-5'-1'-(1H-indol-3-ylmethyl)-3'-methyl-imidazolidine-2',4'-dione] were assayed against sst1, sst3, and sst4 for biochemical binding using Somatostatin-14 as a reference according to the following protocols previous aught in the specification.

|  | $IC_{50}$ | $K_i$ | $n_H$ |
|---|---|---|---|
| Compound A |  |  |  |
| Somatostatin sst1 |  |  |  |
| Compound A | 6.39 μM | 6.07 μM | 0.433 |
| Somatostatin-14 | 8.85 nM | 8.4 nM | 0.747 |
| Somatostatin sst3 |  |  |  |
| Compound A | 6.59 μM | 5.85 μM | 0.564 |
| Somatostatin-14 | 0.717 nM | 0.637 nM | 0.775 |
| Somatostatin sst4 |  |  |  |
| Compound A | 6 μM | 5.27 μM | 0.504 |
| Somatostatin-14 | 5.8 nM | 5.1 nM | 1.02 |
| Compound B |  |  |  |
| Somatostatin sst1 |  |  |  |
| Compound B | 3.25 μM | 3.09 μM | 0.62 |
| Somatostatin-14 | 8.21 nM | 7.8 nM | 0.628 |
| Somatostatin sst3 |  |  |  |
| Compound B | 5.84 μM | 5.18 μM | 0.722 |
| Somatostatin-14 | 0.444 nM | 0.394 nM | 0.73 |

Radioligand Assay measured for sst1, sst3, and sst4 comparing CBE1 (A) against Somatotstatin-14

Example 32

Determination of Functional Activity

This example teaches representative compounds of the present invention that have activity agonist to a receptor that is known to be associated with various therapeutic disorders.

Compounds A and B from the preceding example were assayed against sst2 human ileum tissue and found to have useful agonist activity to sst2 receptor.

| Species | Conc. μM | $EC_{50}/C_{50}$ | % Ag |
|---|---|---|---|
| Compound A | ileum, gp | 3 | 2.9 | 58 |
| Compound B | ileum, gp | 100 | 33.1 | 114 |

Example 33

Preparation of 7-Benzyloxy-3,4-dihydro-2H-quinoline-1-carboxylic acid benzyl ester-4-spiro-5'-3'-[2-(1H-indol-3-yl)-ethyl-1-carboxylic acid tert-butyl ester]-imidazolidine-2',4'-dione 33A: Preparation of a Compound of Formula I, where $R^1$ is benzyl, $R^2$, is carboxylic acid benzyl ester, $R^3$ is 2(1H-indol-3-yl)ethyl, and $R^4$ is hydrogen.

To a solution of Compound 5 (where $R^1$ is benzyl, and $R^{2A}$ is benzyl; 1 g, 2.1 mmol) in anhydrous DMF (5 mL) CSHCO$_3$ (850 mg, 4.3 mmol) was added followed by 3-(2-bromo-ethyl)-indole-1-carboxylic acid tert-butyl ester (780 mg, 2.4 mmol). The reaction was stirred at room temperature for 5 h. The reaction mixture was quenched with water and extracted with EtOAc (3×50 mL). The combined extracts were washed, dried and evaporated. Chromatography using DCM/ETOAc 9:1 gave 7-Benzyloxy-3,4-dihydro-2H-quinoline-1-carboxylic acid benzyl ester-4-spiro-5'-3'-[2-(1H-indol-3-yl)-ethyl-1-carboxylic acid tert-butyl ester]-imidazolidine-2',4'-dione (830 mg, 55% yield). $^1$H NMR (CDCl$_3$) δ: 8.12 (bs, 1H), 7.63 (d, 1H), 7.48 (bs, 1H), 7.46 (s, 1H), 7.38 (m, 11H), 3.31 (m, 1H), 6.68 (d, 1H), 6.58 (dd, 1H), 5.45 (s, 1H), 5.25 (s, 2H), 4.8 (s, 2H), 4.23 (m, 1H), 3.92 (m, 3H), 3.11 (m, 2H), 2.23 (m, 1H), 2.02 (m, 1H), 1.63 (s, 9H);. ESI-MS: m/z 699 [M–H]$^-$.

Example 34

Preparation of 7-Benzyloxy-3,4-dihydro-2H-quinoline-1-carboxylic acid benzyl ester-4-spiro-5'-3'-[2-(indol-3-yl-ethyl)-1-carboxylic acid tert-butyl ester]1'-methyl-imidazolidine-2',4'-dione 34A: Preparation of a Compound of Formula I, where $R^1$ is benzyl, $R^2$ is carboxylic acid benzyl ester, $R^3$ is (indol-3-yl-ethyl)-1 carboxylic acid tert-butyl ester, and $R^4$ is methyl.

Following the procedure taught in Example 10C, and using methyl iodide as the alkylating agent. The desired compound 7-Benzyloxy-3,4-dihydro-2H-quinoline-1-carboxylic acid benzyl ester-4-spiro-5'-3'-[2-(indol-3-yl-ethyl)-1-carboxylic acid tert-butyl ester]-1'-methyl-imidazolidine-2',4'-dione was obtained in 92% yield. $^1$H NMR (CDCl$_3$) δ: 8.2 (bs, 1H), 7.62 (d, 1H); 7.51 (s, 1H), 7.45 (s, 1H), 7.38 (m, 10H), 7.31 (m, 1H), 6.59 (m, 2H), 5.25 (q, 2H), 4.90 (s, 2H), 4.23 (m, 1H), 4.15 (m, 1H), 3.38 (m, 2H), 3.11 (m, 2H), 2.68 (s, 3H), 2.09 (m, 1H), 2.00 (m, 1H), 1.62 (s, 9H); ESI-MS m/z 732 [M+NH$_4$]$^+$.

Example 35

Preparation of 7-Phenoxy-3,4-dihydro-2H-quinoline-4-spiro-5'-3'-(1H-indol-3-ylmethy-1-carboxylic acid tert-butyl ester)-1'-methyl-imidazolidine-2',4'-dione 35A: Preparation of Compound 8 where $R^1$ is phenyl, $R^3$ is 1H-indol-3-ylmethy-1-carboxylic acid tert-buty ester, and $R^4$ is methyl.

A well stirred solution of 12A (220 mg, 0.32 mmol), and ammonium formate (180 mg, 0.96 mmol) in 7 mL of MeOH in a capped vial was treated with solid 10% Pd/C (0.1 g). The mixture was heated at 60° C. for 1 h with stirring, filtered through a celite bed, washed with MeOH, and concentrated under reduced pressure to afford the desired compound, 7-Phenoxy-3,4-dihydro-2H-quinoline-4-spiro-5'-3'-(1H-indol-3-ylmethy-1-carboxylic acid tert-butyl ester)-1'-methyl-imidazolidine-2',4'-dione (180 mg, 100% yield). 1H NMR (CDCl$_3$) δ: 8.10 (m, 2H), 7.76–7.70 (m, 2H), 7.32 (m, 9H), 6.52 (d, J=7.0 Hz 1H), 6.16 (m, 2H), 6.83 (m, 2H), 4.00 (m, 1H), 3.8 (bs, 1H), 3.32 (m, 1H), 2.27 (s, 3H), 1.96 (m, 2H), 1.48 (s, 9H); ESI-MS m/z 553 [M+H]$^+$.

35B: Preparation of a Compound 8, where $R^1$ is hydrogen, $R^2$ is hydrogen, $R^3$ is 2(1H-indol-3-yl)-ethyl-1-carboxylic acid tert-butyl ester, and $R^4$ is methyl.

Following the procedure taught in Example 35A, the desired compound 7-Hydroxy-3,4-dihydro-2H-quinoline-4-spiro-5'-3'-[2-(1H-indol-3-yl)-ethyl-1-carboxylic acid tert-butyl ester]-1'-methyl-imidazolidine-2',4'-dione was obtained at 90% yield. $^1$H NMR (CDCl$_3$) δ: 7.66 (d, J=9 Hz, 1H), 7.45 (d, J=9 Hz, 1H), 7.35 (s, 1H), 7.30 (m, 12H), 6.55 (d, J=9 Hz, 1), 6.24 (m, 2H), 3.89 (m, 3H), 3.29 (m, 1H), 3.07 (m, 2H), 2.79 (s, 3H), 2.40 (m, 1H), 1.86 (m, 1H), 1.64 (s, 9H); ESI-MS m/z: 491 [M+H]$^+$.

Example 36

Preparation of 7-Phenoxy-3'-4'-dihydro-2H-quinoline-1-[(methylpiperidine-4-yl)-carboxylic acid tert butyl ester]-4-spiro-5'-1'-(1H-indole-3yl-methyl)-3'-methyl-imidazoline-2'-4'-dione 36A: Preparation of Compound of Formula I, where $R^1$ is phenyl, $R^2$ is 4-methylpiperidinyl, $R^3$ is methyl, and $R^4$ is (1H-indol-3-yl)methyl.

Following the procedure taught in Example 24A and using 4-formyl-piperidine-1-carboxylic acid tert-butyl ester, the desired compound 7-Phenoxy-3'-4'-dihydro-2H-quinoline 1-[(methylpiperidine-4-yl)-carboxylic acid tert butyl ester]-4-spiro-5'-1'-(1H-indole-3yl-methyl)-3'-methyl-imidazoline-2'-4'-dione was obtained at 78% yield; $^1$H NMR (CDCl$_3$) δ: 8.2 (bs, 1H), 7.36 (m, 1H), 7.19 (m, 7H), 6.71 (d, J=8.7 Hz, 1H), 6.26 (m, 2H), 5.15 (m, 1H), 4.11 (m, 3H), 3.11 (s, 3H), 2.98 (m, 1H), 2.67 (m, 1H), 2.13 (m, 1H), 1.64 (m, 11H), 1.56 (s, 9H); ESI-MS m/z 650 [M+H]$^+$, 672 [M+Na]$^+$.

Example 37

Preparation of 7-Phenoxy-3'-4'-dihydro-2H-quinoline-1-(methylpiperidine-4-yl)-4-spiro-5'-1'-(1H-indol-3ylmethyl)-3'-methyl-imidazoline-2'-4'-dione 37A: Preparation of Compound of Formula I, where $R^1$ is phenyl, $R^2$ is methylpiperidine-4-yl, $R^3$ is methyl, and $R^4$ is 1H-indole-3-ylmethyl.

Following the procedure taught in Example 28, the desired compound 7-Phenoxy-3'-4'-dihydro-2H-quinoline 1-(methylpiperidine-4-yl)-4-spiro-5'-1'-(1H-indole-3yl-methyl)-3'-methyl-imidazoline-2'-4'-dione was obtained in 58% yield; $^1$H NMR (CDCl$_3$) δ: 7.58 (m, 1H), 7.35 (m, 11H), 6.75 (d, J=8.7 Hz 1H), 6.69 (bs, 1H), 6.28 (m, 1H), 5.09 (m, 1H), 4.16 (d, J=15 Hz, 1H), 4.03 (m, 1H), 3.12 (s, 3H), 3.08 (m, 2H), 2.58 (m, 2H), 1.88 (m, 4H), 1.58 (m, 4H), 1.14 (m, 2H); ESI-MS m/z 450 [M+H]$^+$.

Example 38

Preparation of 7-(Tolyloxy)-3'-4'-dihydro-2H-quinoline-5'-1'-(1H-indol-3-yl-methyl)-3'-methy-imidazolidine-2'4'-dione 38A: Preparation of a compound of Formula I where $R^1$ is tolyloxy, $R^2$ is hydrogen, $R^3$ is methyl, $R^4$ is (1H-indol-3-ylmethyl).

A mixture of 7-hydroxy-3,4-dihydro-2H-quinoline-4-spiro-5'-1'-(1H-indol-3-yl)-methyl)-3'-methyl-imidazolidine-2',4'-dione, (80 mg, 0.21 mmol), Cu(OAc)$_2$ (78 mg, 0.40 mmol), p-tolyl boronic acid (60 mg, 0.44 mmol) and 20 mg of powdered 4 Å molecular sieves in 2 mL of anhydrous CH$_2$Cl$_2$ in a capped vial was added to triethylamine (58 μL, 0.410 mmol) in an atmosphere of air The mixture was stirred vigorously at room temperature for 24 h (during which the color was observed changing from blue to green) and filtered through silica bed, washing with CHCl$_3$/MeOH (10:1). Chromatography of the filtrate on silica gel (Hexane/EtOAc 3:1) afforded 7-(Tolyloxy)-3'-4'-dihydro-2H-quinoline-5'-1'-(1H-indol-3-yl-methyl)-3'-methy-imidazolidine-2'4'-dione in 35% yield. $^1$H NMR (CDCl$_3$) δ: 8.02 (bs, 1H), 7.69 (m, 1H), 7.32 (m, 5H), 7.08 (m, 2H0, 6.67 (d, J=8.4 Hz, 1H), 6.18 (m, 2H), 5.07 (d, J=15.6 Hz, 1H), 4.25 (d, J=15.5 Hz, 1H), 3.84 (m, 2H), 3.11 (s, 3H), 2.34 (s, 3H), 2.15 (m, 1H), 1.78 (m, 1H); ESI-MS m/z 467 [M+H]$^+$.

Example 39

Preparation of 7-Tolyxoy-3'-4'-dihydro-2H-quinoline-1-(4-butan-1yl-benzyl carbamic acid tert-butyl ester)-4-spiro-5'-1'-(1H-indol-3-yl-methyl)-3'-methy-imidazolidine-2'4'-dione 39A: Preparation of a Compound of Formula I, where $R^1$ is tolyl, $R^2$ is 4-butan-1-yl-benzyl carbamic acid tert-butyl ester, $R^3$ is methyl, and $R^4$ is (1H-indol-3-yl)methyl.

Following the procedure taught in Example 24, the desired compound, 7-Tolyxoy-3'-4'-dihydro-2H-quinoline-1-(4-butan-1yl-benzyl carbamic acid tert-butyl ester)-4-spiro-5'-1'-(1H-indol-3-yl-methyl)-3'methy-imidazolidine-2'4'-dione, was obtained in 38% yield; $^1$H NMR (CDCl$_3$) δ: 7.68 (m, 1H), 7.46 (m, 13H), 7.04 (d, J=8.3 Hz, 1H), 6.31 (bs, 1H), 6.12 (m, 1H), 5.01 (d, J=15.6 Hz, 1H), 4.32 (m, 2H), 4.16 (d, J=15.6 Hz, 1H), 3.98 (m, 1H), 3.66 (m, 3H), 3.10 (m, 5H, 2.34 (s, 3H), 2.04 (m, 1H, 1.77 (m, 5H), 1.45 (s, 9H); ESI-MS: m/z 728 [M+H]$^+$.

Example 40

Preparation of 7-Tolyloxy-3'-4'-dihydro-2H-quinoline-1-(4-benzyl amino-butan-1yl)-4-spiro-5'-1'-(1H-indol-3-yl-methyl)-3'methyl-imidazolidine-2'4'-dione 40A: Preparation of a Compound of Formula I, where $R^1$ is tolyloxy, $R^2$ is 4-benzyl amino-butan-1-yl), $R^3$ is methyl, and $R^4$ is (1H-indol-3-yl)methyl.

Following the procedures taught in Example 28 the desired compound, 7-Tolyloxy-3'-4'-dihydro-2H-quinoline-1-(4-benzyl amino-butan-1yl)-4-spiro-5'-1'-(1H-indol-3-yl-methyl)-3'-methyl-imidazolidine-2'4'-dione, was obtained in 68% yield. $^1$H NMR (CDCl$_3$) δ: 8.02 (bs, 1H), 7.69 (m, 1H), 7.32 (m, 5H), 7.08 (m, 2H), 6.67 (d, J=8.4 Hz, 1H), 6.18 (m, 2H), 5.07 (d, J=15.6 Hz, 1H), 4.25 (d, J=15.5 Hz, 1H), 3.84 (m, 2H), 3.70 (m, 1H), 3.28 (m, 1H), 3.08 (s, 3H), 2.79 (m, 1H), 2.60 (m, 4H), 2.34 (s, 3H), 2.15 (m, 1H), 1.78 (m, 1H); ESI-MS m/z 467 [M+H]$^+$.

Example 41

Preparation of 7-Tolyloxy-3'-4'-dihydro-2H-quinoline-1-(aminobutan-1yl)-4-spiro-5'-1'(1H-indol-3-yl-methyl)-3'-methyl-imidazolidine-2'4'-dione

41A: Preparation of a Compound of Formula I, where $R^1$ is tolyl, $R^2$ is 4-butylamino-1-yl, $R^3$ is methyl, and $R^4$ is 1H-indol-3-ylmethyl.

Following the procedure taught in Example 26A, the desired compound 7-Tolyloxy-3'-4'-dihydro-2H-quinoline-1-(amino butan-1yl)-4-spiro-5'-1'-(1H-indol-3-yl-methyl)-3'methyl-imidazolidine-2'4'-dione was obtained in 43% yield; $^1$H NMR (CDCl$_3$) δ: 9.30 (bs, 1H), 7.65 (m, 1H), 7.30 (m, 1H), 7.03 (m, 5H), 6.90 (m, 3H), 6.65 (m, 1H), 6.29 (m, 1H), 6.10 (m, 2H), 5.29 (m, 1H), 4.18 (m, 1H), 3.47 (m, 1H), 3.14 (s, 3H), 2.82 (m, 2H), 2.54 (m, 3H), 2.33 (s, 3H), 1.62 (m, 4H); ESI-MS m/z 538 [M+H]$^+$.

Example 42

Preparation of 7-Hydroxy-3'-4'-dihydro-2H-quinoline-1-(butyl-1-yl-benzyl carbamic acid tert butyl ester)-4-spiro-5'-1'-methyl-3'[2(-1H-indol-3-yl)-ethyl-1-carboxylic acid tert-butyl ester]-imidazolidine-2'4'-dione

42A: Preparation of a Compound of Formula I, where $R^1$ is hydrogen, $R^2$ is butyl-1-yl-benzyl carbamic acid tert butyl ester, $R^3$ is 2(1H-indol-3-yl)ethyl, and $R^4$ methyl.

Compound 35B was reacted with N-benzyl-N-(tert butoxycarbonyl)-4-amino-1-butanal following the procedures taught in Example 24A to provide the -desired compound, 7-Hydroxy-3'-4'-dihydro-2H-quinoline-1-(butyl-1-yl-benzyl 4-carbamic acid tert butyl ester)-4-spiro-5'-1'-methyl-3'[2(-1H-indol-3-yl)-ethyl-1-carboxylic acid tert-butyl ester]-imidazolidine-2'4'-dione in 65% yield. $^1$H NMR (CDCl$_3$) δ: 8.14 (d, J=8.3 Hz, 1H), 7.64 (d, J=8.6 Hz, 1H), 7.44 (s, 1H), 7.32 (m, 7H), 6.98 (m, 1H), 6.47 (m, 1H), 6.08 (m, 1H), 4.43 (s, 2H), 3.83 (m, 2H), 3.63 (m, 2H), 3.26 (m, 3H), 3.05 (m, 3H), 2.77 (s, 3H), 2.15 (m, 1H), 1.87 (m, 1H), 1.64 (s, 9H), 1.56 (m, 15H) ESI-MS m/z 752 [M+H]$^+$.

Example 43

Preparation of 7-Tolyloxy-3'-4'-dihydro-2H-quinoline-1-(butyl-1-yl-benzyl carbamic acid tert butyl ester)-4-spiro-5'-1'-methyl-3'-[2(-1H-indol-3-yl)-ethyl-1-carboxylic acid tert-butyl ester]-imidazolidine-2'4'-dione

43A: Preparation of a Compound of Formula I, where $R^1$ is tolyl, $R^2$ is butyl-1-yl benzyl carbamic acid tert butyl ester, $R^3$ is 2(1H-indol-3-yl)-ethyl-1-carboxylic acid tert-butyl ester, and $R^4$ is methyl.

Compound 38A (where $R^1$ is tolyl, $R^2$ is H, $R^3$ is 2(1H-indol-3-yl)-ethyl-1-carboxylic acid tert-butyl ester, and $R^4$ is methyl was treated with N-benzyl-N-(tert butoxycarbonyl)-4-amino-1-butanal as described for in example 42A to provide the desired compound, 7-Tolyloxy-3'-4'-dihydro-2H-quinoline-1-(butyl-1-yl-benzyl carbamic acid tert butyl ester)-4-spiro-5'-1'-methyl-3'-[2(-1H-indol-3-yl)-ethyl-1-carboxylic acid tert-butyl ester]-imidazolidine-2',4'-dione in 90%. $^1$H NMR (CDCl$_3$) δ: 8.12 (d, J=7.8 Hz, 1H), 7.65 (d, J=7.8 Hz, 1H), 7.44 (s, 1H), 7.35 (m, 7H), 7.12 (m, 2H), 6.89 (m, 2H), 6.52 (d, J=8.4 Hz, 1H), 6.26 (m, 1H), 6.10 (m, 1H), 4.41 (s, 2H), 3.90 (m, 3H), 3.07 (m, 7H), 2.74 (s, 3H), 2.31 (s, 3H), 1.84 (m, 1H), 1.79 (m, 2H), 1.63 (s, 18H); ESI-MS m/z 842 [M+H]$^+$, 864 [M+Na]$^+$.

Example 44

Preparation of 7-Tolyloxy-3'-4'-dihydro-2H-quinoline-1-(4-benzyl amino-butan-1yl)-4-spiro-5'-1'-methyl-3'[2(-1H-indol-3-yl)-ethyl-1-carboxylic acid tert-butyl ester]-imidazolidine-2'4'-dione

44A: Preparation of a Compound of Formula I, where $R^1$ is tolyl, $R^2$ is 4-benzyl amino-butan-1-yl, $R^3$ is 2-(1H-indo-3-yl)-ethyl-1-carboxylic acid tert-butyl ester, and $R^4$ is methyl.

Following the procedure taught in Example 40A 7-tolyloxy-3'-4'-dihydro-2H-quinoline-1-(butyl-1-yl-benzyl carbamic acid tert butyl ester)-4-spiro-5'-1'-methyl-3'-[2(-1H-indol-3-yl)-ethyl-1-carboxylic acid tert-butyl ester]-imidazolidine-2',4'-dione was treated with TFA to provide the desired compound, 7-tolyloxy-3'-4'-dihydro-2H-quinoline-1-(4-benzyl-amino-butan-1yl)-4-spiro-5'-1'-methyl-3'-[2(1H-indol-3-yl)-ethyl-1-carboxylic acid tert-butyl ester]-imidazolidine-2'4'-dione, in 89%; yield. $^1$H NMR (CDCl$_3$) δ: 8.01 (bs, 1H), 7.69 (m, 1H), 7.33 (m, 6H), 7.14 (m, 5H), 6.92 (m, 2H), 6.39 (m, 1H), 6.27 (bs, 1H), 6.01 (m, 1H), 4.23 (bs., 2H), 3.84 (m, 3H), 3.23 (m, 4H), 2.74 (s, 3H), 2.63 (m, 2H), 2.32 (s, 3H), 2.06 (m, 2H), 1.58 (m, 5H); ESI-MS m/z 642 [M+H]$^+$.

Example 45

Preparation of 7-Tolyloxy-3'-4'-dihydro-2H-quinoline-1-(4-amino-butan-1yl)-4-spiro-5'-1'-methyl-3'[2-(1H-indol-3-yl)-ethyl]-imidazolidine-2'4'-dione

45A: Preparation of a Compound of Formula I, where $R^1$ is tolyl, $R^2$ is 4-amino-butan-1-yl, $R^3$ is 2-(1H-indol-3-yl)-ethyl] and $R^4$ is methyl.

Following the procedure taught in Example 41A, 7-tolyloxy-3'-4'-dihydro-2H-quinoline-1-(4-benzyl-amino-butan-1yl)-4-spiro-5'-1'-methyl-3'-[2(1H-indol-3-yl)-ethyl-1-carboxylic acid tert-butyl ester]-imidazolidine-2'4'-dione was hydrogenated to provided the desired compound, 7-Tolyloxy-3'-4'-dihydro-2H-quinoline-1-(4-amino-butan-1yl)-4-spiro-5'-1'-methyl-3'[2-(1H-indol-3-yl)-ethyl]-imidazolidine-2'4'-dione with a yield of 83%. $^1$H NMR (CDCl$_3$) δ 7.67 (m, 1H), 7.19 (m, 7H), 6.89 (m, 2H), 6.41 (m, 1H), 6.26 (m, 2H), 5.99 (m, 1H), 3.84 (m, 2H), 3.26 (m, 3H), 2.73 (s, 2H), 2.62 (bs, 1H), 2.32 (s, 3H), 1.70 (m, 10H); ESI-MS m/z 552 [M+H]$^+$.

Example 46

Preparation of 7-(Benzo-[1,3]-dioxol-5-yloxy)-3'-4'-dihydro-2H-quinoline-1-(butyl-1-yl-benzyl carbamic acid tert butyl ester)-4-spiro-5'-1'-methyl-3'[2-(-1H-indol-3-yl)-ethyl-1-carboxylic acid tert-butyl ester]-imidazolidine-2'4'-dione

46A: Preparation of a Compound of Formula I, where $R^1$ is benzo[1,3]dioxol, $R^2$ is 4-benzyl amino-butan-1-yl, $R^3$ is (1H-indol-3-yl)ethyl, and $R^4$ is methyl.

Following the procedures taught for Example 38A, a mixture of 7-hydroxy-3,4-dihydro-2H-quinoline-4-spiro-5'-1'-(1H-indol-3-yl)-methyl)-3'-methyl-imidazolidine-2',4'-dione, was treated with benzo-[1,3]dioxo-5-yl-boronic acid to provide the desired compound 7-(Benzo-[1,3]-dioxol-5-yloxy)-3'-4'-dihydro-2H-quinoline-1-(butyl-1-yl-benzyl carbamic acid tert butyl ester)-4-spiro-5'-1'-methyl-3'[2-(-1H-indol-3-yl)-ethyl-1-carboxylic acid tert-butyl ester]-imidazolidine-2'4'-dione in 62% yield. $^1$H NMR (CDCl$_3$) δ: 8.12 (m, 1H), 7.65 (d, J=7.8 Hz, 1H), 7.44 (s, 1H), 7.35 (m, 7H), 6.75 (d, J=9Hz; 1H), 6.57 (m, 1H), 6.49 (m, 2H), 6.24 (bs, 1H), 6.05 (m, 1H), 5.97 (s, 2H), 4.44 (s, 2H), 3.87 (m, 3H), 3.20 (5H), 2.96 (m, 2H), 2.74 (s, 3H), 2.14 (m, 1H), 1.84 (m, 1H), 1.64 (bs, 20H); ESI-MS m/z 872 [M+H]$^+$.

Example 47

Preparation of 7-(Benzo-[1,3]-dioxol-5-yloxy)-3'-4'-dihydro-2H-quinoline-1-(4-benzyl amino-butan-1-yl)-4-spiro-5'-1'-methyl-3'[2-(-1H-indol-3-yl)-ethyl]-imidazolidine-2'4'-dione 47A: Preparation of a Compound of Formula I, where $R^1$ is benzo[1,3]dioxol, $R^2$ is 4-benzyl amino-butan-1-yl, $R^3$ is (1H-indol-3-yl)ethyl, and $R^4$ is methyl.

Following the procedures taught in Example 40A, the desired compound 7-(Benzo-[1,3]-dioxol-5-yloxy)-3'-4'-dihydro-2H-quinoline-1-(4-benzyl amino-butan-1yl)-4-spiro-5'-1'-methyl-3'-[2-(-1H-indol-3-yl)-ethyl]-1-carboxylic acid tert-butyl ester]-imidazolidine-2'4'-dione was obtained in 87% yield. $^1$H NMR (CDCl$_3$) δ: 8.08 (s, 1H), 7.68 (m, 1H), 7.32 (m, 6H), 7.16 (m, 4H), 6.75 (m, 1H), 6.56 (m, 1H), 6.48 (m, 1H), 6.38 (m, 1H), 6.25 (m, 1H), 5.98 (s, 2H), 3.87 (m, 5H), 3.21 (m, 5H), 2.71 (s, 3H), 2.65 (m, 2H), 2.06 (m, 2H), 1.62 (m, 3H); ESI/MS: m/z 672 [M+H]$^+$.

Example 48

Preparation of 7-(Benzo[1,3]dioxol-5-yloxy)-3'-4'-dihydro-2H-quinoline-1-(4-amino-butan-1-yl)-4-spiro-5'-1'-methyl-3'[2-(-1H-indol-3-yl)-ethyl-1-carboxylic acid tert-butyl ester]-imidazolidine-2'4'-dione 48A: Preparation of a Compound of Formula I, where $R^1$ is benzo[1,3]dioxol, $R^2$ is 4-butylamino-1-yl, $R^3$ is 2-(1H-indol-3-yl)ethyl, and $R^4$ is methyl.

Following the procedure taught in Example 41A the desired compound 7-(Benzo-[1,3]-dioxol-5-yloxy)-3'-4'-dihydro-2H-quinoline-1-(4-amino-butan-1yl)-4-spiro-5'-1'-methyl-3'[2-(-1H-indol-3-yl)-ethyl]-imidazolidine-2'4'-dione was obtained in 76% yield. $^1$H NMR (CDCl$_3$) δ: 7.60 (m, 2H), 7.21 (m, 6H), 6.79 (m, 1H), 6.46 (m, 4H), 6.30 (m, 1H), 5.96 (s, 2H), 3.13 (m, 2H), 2.77 (m, 6H), 1.63 (m, 6H), 1.32 (m, 6H); ESI-MS m/z 582 [M+H]$^+$.

Example 49

Preparation of 7-Phenoxy-3,4-dihydro-2H-quinoline-1-(4-oxo-1-butylamino)-4-spiro-5'-3'-methyl-1'-(1H-indol-3-yl-methyl)-imidazolidine-2',4'-dione 49A: Preparation of a Compound of Formula I, where $R^1$ is Ph, $R^2$ is 4-oxo-1yl-N-benzyl-butyl-carbamic acid tert-butyl ester, $R^3$ is methyl-and $R^4$ is 1H-indol-3-yl-methyl.

To a well stirred solution of Compound 23B $R^1$ is Ph, $R^2$ is hydrogen, $R^3$ is methyl-and $R^4$ is 1H-indol-3-yl-methyl: (0.039 g, 0.102 mmol) and N-benzyl-N-(tert butoxycarbonyl)-4-amino-1-butanoic acid (0.036 g, 0.123 mmol) in anhydrous CH$_2$Cl$_2$ (2 mL), 1-(3-dimethylaminopropyl)-3-ethycarbodiimide (0.06 g, 0.31 mmol), disopropylethyl amine (1 eq), dimethyl amino pyridine (catalytic amount) were added. The reaction mixture was stirred at R.T. for 24 h. After this time the mixture was quenched with a saturated solution NaHCO$_3$ (5 mL and extracted with CH$_2$Cl$_2$ (3×10 mL). The organic layer was washed with water, brine and dried over Na$_2$SO$_4$. The crude was further purified by chromatography on silica gel using 7:3 hexanes/ethyl acetate mixtures as eluent to give 7-Phenoxy-3,4-dihydro-2H-quinoline-1-(4-oxo-1-yl-butyl-carbamic acid tert-butyl ester)-4-spiro-5'-3'-methyl-1'-(1-H-indol-3-yl-methyl)-imidazolidine-2',4'-dione (0.03 g, 46% yield was obtained as off white solid. $^1$H NMR (CDCl$_3$) δ 8.12 (bs, 1H); 7.62–7.06 (m, 14H); 7.13–7.96 (m, 5H); 4.54–4.28 (m, 4H); (bs, 3.80–3.77 (m, 2H); 3.15–2.98 (m, 2H); 2.49 (s, 3H); 2.57–2.44 (m, 2H); 2.22 (bs, 1H); 2.15–2.07 (m, 1H); 1.87–1.82 (m, 2H); 1.65 (s, 9H); 1.28–1.17 (m, 2H). ELSD-MS 727 [M+H]$^+$.

49B: Preparation of a Compound of Formula I, where $R^1$ is Ph, $R^2$ is 4-benzylamino-butan-1-one, $R^3$ is methyl and $R^4$ is 1H-indol-3-yl-methyl.

To a solution of 7-Phenoxy-3,4-dihydro-2H-quinoline-1-(4-oxo-1-yl-butyl-carbamic acid tert-butyl ester)-4-spiro-5'-3'-methyl-1'-(1-H-indol-3-yl-methyl)-imidazolidine-2',4'-dione (0.023 g, 0.031 mmol) in anhydrous DCM (5 mL) stirred at room temperature TFA (1.0 mL) was added drop wise. The reaction mixture was stirred at this temperature for 30 min and then it was diluted with 0.1N NaOH and extracted with DCM (3×10 mL). The organic was washed with water, brine, dried over Na$_2$SO$_4$ and evaporated to dryness under vacuum. The crude was purified over a small silica gel column using 9.6:06:0.1 CH$_2$Cl$_2$-MeOH-NH$_4$ mixture as eluent to afford 7-phenoxy-3,4-dihydro-2H-quinoline-1-(4-benzylamino-butyl-1-one)-4-spiro-5'-1'-(1H-indol-3-ylmethyl)-3'-methyl-imidazoline-2',4'-dione (0.018 g 90%) as thick oil. $^1$H NMR (CDCl$_3$) δ 9.77 (bs, 1H); 9.40 (bs, 1H); 8.29 (m, 1H); 7.60 (m, 1H); 7.46 (m, 12H); 7.15 (m, 1H); 6.94 (m, 1H); 6.61 (m, 1H), 6.32 (d, 1H); 5.84 (m, 1H); 4.60 (m, 2H); 4.08 (bs, 2H); 3.90 (m, 1H); 3.42 (m, 1H); 3.11 (s, 3H); 3.04 (m, 1H); 3.27 (m, 1H); 2.61 (m, 1H); 2.15 (m, 6H). ELSD-MS: m/z 628 [M+H]$^+$.

49C: Preparation of a Compound of Formula I, where $R^1$ is Ph, $R^2$ is 4-amino-1-yl-butan-1-one, $R^3$ is methyl and $R^4$ is 1H-indol-3-ylmethyl.

Using the procedure described for Example 41A 7-phenoxy-3,4-dihydro-2H-quinoline-1-(4-amino-butyl-1-one)-4-spiro-5'-1'-(1H-indol-3-ylmethyl)-3'-methyl-imidazoline-2',4'-dione compound 50C was obtained as brownish solid (90% yield). $^1$H NMR (CDCl$_3$) δ 8.16 (m, 1H) 7.66 (m, 1H); 7.36–7.00 (m, 12H); 6.68 (m, 1H); 6.21 (m, 2H), 5.24 (d, 1H); 4.27 (d, 1H); 3.84 (m, 1H); 3.26 (m, 1H); 3.05 (s, 3H); 2.42 (m, 1H); 2.13 (m, 1H); 2.01 (m, 1H); 1.73 (m, 1H); 1.39 (m, 4H). ELSD-MS m/z 538 [M+H]$^+$.

Example 50

Preparation of 7-Hydroxy-3,4-dihydro-2H-quinoline-1-(4-amino-1-yl-butan)-4-spiro-5'-3'[2 (1H-indol-3-yl-ethyl)-1'-methyl-imidazolidine-2',4'-dione 50A: Preparation of a Compound of Formula I, where $R^1$ is hydroxy, $R^2$ is butyl-1-yl-benzyl carbamic acid tert butyl ester, $R^3$ is [2(1H-indol-3-yl)-ethyl]-1-carbamic acid tert-butyl ester and $R^4$ is methyl Using the procedure described for Example 24A, 7-hydroxy-3,4-dihydro-2H-quinoline-4-spiro-5'-1'-methyl-3'[2-(1H-indol-3-yl-ethyl]-1-carboxylic acid tert butyl ester was converted to 7-hydroxy-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2'4'-dione in 65% yield. $^1$H NMR (CDCl$_3$) δ: 8.14 (d, J=8.3 Hz, 1H), 7.64 (d, J=8.6 Hz, 1H), 7.44 (s, 1H), 7.32 (m, 7H), 6.98 (m, 1H), 6.47 (m, 1H), 6.08 (m, 1H), 4.43 (s, 2H), 3.83 (m, 2H), 3.63 (m, 2H), 3.26 (m, 3H), 3.05 (m, 3H), 2.77 (s, 3H), 2.15 (m, 1H), 1.87 (m, 1H), 1.64 (s, 9H), 1.56 (m, 15H); ESI-MS m/z 752 [M+H]$^+$.

50B: Preparation of a Compound of Formula I, where $R^1$ is hydroxy, $R^2$ is 4-benzylamino-butan-4yl, $R^3$ is [2-(1H-indol-3-yl)-ethyl] and $R^4$ is methyl.

Using the procedure described for Example 25A 7-hydroxy-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2'4'-dione was converted into 7-hydroxy-3,4-dihydro-2H-quinoline-1-(N-benzyl amino-butan-4-yl)-4-spiro-5'-1'-methy-3'-[2-(1H-indol-3-yl-ethyl]-imidazoline-2'4'-dione in 68% yield. ELSD-MS m/z 552 [M+H]+.

50C: Preparation of a Compound of Formula I, where $R^1$ is hydroxy, $R^2$ is 4-butylamino-1-yl, $R^3$ is [2-(1H-indol-3-yl)-ethyl] and is $R^4$ is methyl Using the procedure described for Example 26A 7-hydroxy-3,4-dihydro-2H-quinoline-1-(N-benzyl amino-butan-4-yl)-4-spiro-5'-1'-methy-3'-[2-(1H-indol-3-yl-ethyl]-imidazoline-2'4'-dione was converted into 7-hydroxy-3,4-dihydro-2H-quinoline-1-(amino-butan-4-yl)-4-spiro-5'-1'-methy-3'-[2-(1H-indol-3-yl-ethyl]-imidazoline-2'4'-dione in 80% yield. $^1$H NMR (CD$_3$OD) δ: 7.96 (m, 7H), 7.22 (m 3H), 4.03–3.52 (m, 6H), 2.91 (m, 2H), 2.27 (m, 2H), 1.99–1.54 (m, 6H) ELSD-MS m/z 462 [M+H]+.

Example 51

Preparation of 7-(4-Methoxy-phenoxy)-3,4-dihydro-2H-quinoline-1-(4-amino-1-yl-butan)-4-spiro-5'-3'-[2-(1H-indol-3-yl-ethyl)-1'-methyl-imidazolidine-2', 4'-dione 51A: Preparation of a Compound of Formula I, where $R^1$ is (4-methoxy-phenoxy), $R^2$ is butyl-1-yl-benzyl carbamic acid tert butyl ester, $R^3$ is [2(1H-indol-3-yl)-ethyl]-1-carbamic acid tert-butyl ester and $R^4$ is methyl Using the procedure described for Example 43A 7-hydroxy-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2'4'-dione was coupled with 4-methoxy boronic acid to afford 7-(4-methoxy-phenoxy)-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2',4'-dione in 95% yield (based on recovered starting material). $^1$H NMR (CDCl$_3$) δ: 8.12 (m, 1H); 8.09 (m, 1H); 7.62–7.09 (m, 10H); 6.91 (m, 1H); 6.52 (m, 1H); 6.26 (m, 1H); 6.10 (m, 1H); 4.41 (bs, 2H); 3.85 (m, 4H); 3.18 (m, 7H); 2.74 (s, 3H); 1.83 (m, 1H); 1.70–1.45 (m, 29H). ELSD-MS: m/z 858 [M+H]+.

51B: Preparation of a Compound of Formula I, where $R^1$ is (4-methoxy-phenoxy), $R^2$ is N-benzyl-4-aminobutyl-1-yl-, $R^3$ is [2(1H-indol-3-yl)-ethyl] and $R^4$ is methyl Using the procedure described for Example 44A 7-(4-methoxy-phenoxy)-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2',4'-dione was converted into 7-(4-methoxy-phenoxy)-3,4-dihydro-2H-quinoline-1-(4-N-benzyl-aminobutyl-1-yl-)-4-spiro-5'-1'-methy-3'-[2-(1H-indol-3-yl-ethyl]-imidazoline-2',4'-dione in 87% yield. $^1$H NMR (CDCl$_3$) δ: 8.18 (bs, 1H); 7.66 (d, 1H); 7.32 (m, 5H); 7.31–6.85 (m, 8H); 6.37 (d, 1H); 6.22 (bs, 1H); 5.98 (d, 1H); 3.86 (m, 3H); 3.80 (s, 3H); 3.14 (m, 4H); 2.70 (s, 3H); 2.62 (t, 2H); 2.08–2.00 (m, 3H); 1.63–1.48 (m, 6H). ELSD-MS: m/z 658 [M+H]+.

51C: Preparation of a Compound of Formula I, where $R^1$ is 4-methoxy-phenyl, $R^2$ is 4-aminobutyl-1-yl-, $R^3$ is [2(1H-indol-3-yl)-ethyl] and $R^4$ is methyl Using the procedure described for Example 45A 7-(4-methoxy-phenoxy)-3,4-dihydro-2H-quinoline-1-(4-N-benzyl-4-aminobutyl-1-yl-)-4-spiro-5'-1'-methy-3'-[2-(1H-indol-3-yl-ethyl]-imidazoline-2',4'-dione was converted into 7-(4-methoxy-phenoxy)-3,4-dihydro-2H-quinoline-1-(4-aminobutyl-1-yl-)-4-spiro-5'-1'-methy-3'-[2-(1H-indol-3-yl-ethyl]-imidazoline-2'4'-dione in 80% yield. $^1$H NMR (CDCl$_3$) δ: 7.68 (m, 1H); 7.37 (m, 2H); 7.28–6.83 (m, 7H); 6.41 (m, 1H); 6.33 (m, 1H); 6.19 (m, 1H); 3.79 (s, 3H); 3.21 (m, 4H); 2.72 (m, 5H); 2.58 (m, 2H); 2.44 (m, 2H), 1.62 (m, 8H). ELSD-MS: m/z 567 [M+H]+.

Example 52

Preparation of 7-(3,4-Dimethyl-phenoxy)-3,4-dihydro-2H-quinoline-1-(4-amino-1-yl-butan)-4-spiro-5'-3'[2(1H-indol-3-yl-ethyl)-1'-methyl-imidazolidine-2',4'-dione 52A: Preparation of a Compound of Formula I, where $R^1$ is (3,4-dimethyl-phenoxy), $R^2$ is butyl-1-yl-benzyl carbamic acid tert butyl ester, $R^3$ is [2(1H-indol-3-yl)-ethyl]-1-carbamic acid tert-butyl ester and $R^4$ is methyl Using the procedure described for Example 43A 7-hydroxy-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2',4'-dione was coupled with 3,4-dimethyl boronic acid to afford 7-(3,4-dimethyl-phenoxy)-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2'4'-dione in 36% yield. $^1$H NMR (CDCl$_3$) δ: 8.12 (bs, 1H); 7.66 (d, 1H); 7.44 (bs, 1H); 7.31 (m, 4H); 7.07 (m, 2H); 6.98 (d, 1H); 6.82 (m, 3H); 6.71 (m, 2H); 6.50 (bs, 1H); 6.09 (d, 1H); 4.41 (m, 2H); 3.84 (m, 3H); 3.06 (m, 7H); 2.75 (s, 3H); 2.22 (s, 6H); 1.70 (m, 24H). ELSD-MS: m/z 857 [M+H]+.

52B: Preparation of a Compound of Formula I, where $R^1$ is (3,4-dimethyl-phenoxy), $R^2$ is N-benzyl-4-aminobutyl-1-yl-$R^3$ is [2(1H-indol-3-yl)-ethyl] and $R^4$ is methyl.

Using the procedure described for Example 44A 7-(3,4-dimethyl-phenoxy)-3,4-dihydro-2H-quinoline-1-butyl-benzyl carbamic acid tert butyl ester-4-spiro-5'-1'-methy-3'-[2-(1H-indol-3-yl-ethyl]-1-carbamic acid tert butyl ester-imidazoline-2',4'-dione was converted into 7-(3,4-dimethyl-phenoxy)-3,4-dihydro-2H-quinoline-1-(4-N-benzyl-aminobutyl-1-yl-)-4-spiro-5'-1'-methy-3'-[2-(1H-indol-3-yl-ethyl]-imidazoline-2',4'-dione in 73% yield. $^1$H NMR (CDCl$_3$) δ: 8.09 (bs, 1H); 7.7 (d, 1H); 7.32 (m, 4H); 7.11 (m, 4H); 6.79 (m, 4H); 6.39 (m, 1H); 6.28 (m, 1H); 5.99 (m, 1H); 3.86 (m, 4H); 3.20 (m, 4H); 2.73 (s, 3H); 2.63 (m, 2H); 2.22 (s, 6H); 2.07 (m, 2H); 1.62 (m, 6H). ELSD-MS: m/z 656 [M+H]+.

52C: Preparation of a Compound of Formula I, where $R^1$ is 3,4-dimethyl-phenyl, $R^2$ is 4-butylamino-1-yl-, $R^3$ is [2-(1H-indol-3-yl)-ethyl] and $R^4$ is methyl.

Using the procedure described for Example 45A 7-(3,4-dimethyl-phenoxy)-3,4-dihydro-2H-quinoline-1-(4-N-benzyl-4-aminobutyl-1-yl-)-4-spiro-5'-1'-methy-3'-[2-(1H-indol-3-yl-ethyl]-imidazoline-2',4'-dione was converted into 7-(3,4-dimethyl-phenoxy)-3,4-dihydro-2H-quinoline-1-(4-aminobutyl-1-yl-)-4-spiro-5'-1'-methy-3'-[2-(1H-indol-3-yl-ethyl]-imidazoline-2',4'-dione in 65% yield. $^1$H NMR (CDCl$_3$) δ: 7.61 (m, 1H); 7.37 (m, 1H); 7.08 (m, 4H); 6.80 (m, 3H); 6.43 (m, 2H); 6.02 (m, 1H). ELSD-MS: m/z 566 [M+H]+.

Example 53

Preparation of 4-Hydroxymethyl-piperidine-1-carboxylic acid tert-butyl ester

The compound was prepared following the same procedure used for preparing benzyl-(4-hydroxy-butyl)-carbamic acid tert-butyl ester (see Example 17B) at a yield of 80%; $^1$H NMR (CDCl$_3$) δ: 4.13 (m, 2H), 3.50 (m, 2H), 2.70 (m, 2H), 1.86 (m, 1H), 1.74 (m, 3H), 1.48 (s, 9H), 1.15 (m, 2H).

Example 54

Preparation of 4-Formyl-piperidine-1-carboxylic acid tert-butyl ester

The compound was prepared according the procedure described for N-benzyl-N(t-butoxycarbonyl-4-amino-1-butanal (see Example 19) at a yield of 98%; $^1$H NMR (CDCl$_3$) δ: 9.63 (s, 1H), 3.98 (m, 2H), 2.93 (m, 2H), 2.45 (m, 1H), 1.89 (m, 2H), 1.56 (m, 2H), 1.45 (s, 9H).

Example 55

Preparation of 3-(2-Bromo-ethyl)-indole-1-carboxylic acid tert-butyl ester

The compound was prepared according to the procedure described for preparing (4-hydroxy-butyl)-carbamic acid tert-butyl ester (see Example 19) in 87% yield. $^1$H NMR (CDCl$_3$) δ: 8.12 (bs, 1H), 7.50 (m, 2H), 7.30 (m, 2H), 3.63 (t, J=7.5 Hz, 2H), 3.27 (t, J=7.5 Hz, 2H), 1.67 (s, 9H); ESI-MS m/z 324 [M+H]$^+$.

Example 56

Preparation of 7-Phenoxy-3'-4'-dihydro-2H-quinoline-1-(methylpiperidine-4-yl)-4-spiro-5'-1'-methyl 3'-(1H-indol-3-yl-methyl)-imidazolidine-2'4'-dione A compound of Formula I, where R$^1$ is phenyl, R$^2$ is methylpiperidin-4-yl, R$^3$ is (1H-indol-3-yl)methyl, and R$^4$ is hydrogen can be prepared by following the synthetic procedures.

56A: Preparation of 7-Phenoxy-3,4-dihydro-2H-aminoline-1-carboxylic acid benzyl ester-4-spiro-5'-3'-(1H-indol-3-ylmethyl)-imidazolidine-2',4'-dione.

To a solution of Compound 5, where R$^1$ is phenyl and R$^2$ is benzyl in anhydrous DMF (8 mL) at room temperature will be added CsHCO$_3$ (1.2 equivalents). The suspension will be stirred for 10–15 min and then a solution of trimethyl-(1-triisopropylsilanyl)-1-H-indol-3-ylmethyl) ammonium iodide (1.06 eq) in DMF (2 mL), and 1M solution TBAF (1.2 mmol) will be slowly added simultaneously. After the addition, the reaction mixture will be stirred at room temperature for 6–8 h. The mixture will be then quenched with water and extracted with EtOAc (3×30 mL). The combined EtOAc layer will be washed with water, brine, dried over Na$_2$SO$_4$ and evaporated to dryness under vacuum. The resulting residue will be purified by chromatography on silica gel using the suitable mixture of DCM and EtOAc as eluent.

56B: Preparation of 7-Phenoxy-3,4-dihydro-2H-quinoline-1-carboxylic acid benzyl ester-4-spiro-5'-1'-methyl-3'-(1H-indol-3-ylmethyl)-imidazolidine-2',4'-dione.

A solution of 7-Phenoxy-3,4-dihydro-2H-quinoline-1-carboxylic acid benzyl ester-4-spiro-5'-3'-(1H-indol-3-ylmethyl)-imidazolidine-2',4'-dione in DMF, will be treated with solid K$_2$CO$_3$ (1.5 eq.) and methyl iodide (1.5 eq). The reaction mixture will be stirred for 6–8 h at room temperature, and then worked-up using the usual protocol described above. The reaction residue will be purified by chromatography using the suitable DCM/EtOAc solvent mixture as eluent.

56C: Preparation of 7-Phenoxy-3,4-dihydro-2H-guinoline-4-spiro-5'-1'-methyl-3'-(1H-indol-3-ylmethyl)-imidazolidine-2',4'-dione.

A solution of 7-Phenoxy-3,4-dihydro-2H-quinoline-1-carboxylic acid benzyl ester-4-spiro-5'-1'-methyl-3'-(1H-indol-3-ylmethyl)-imidazolidine-2',4'-dione will undergo hydrogenolysis reaction as described in Example 23A.

56D: Preparation of 7-Phenoxy-3'-4'-dihydro-2H-quinoline-1-[(methylpiperidine-4yl)-1carboxylic acid tert-butyl ester]-4-spiro-5'-3'-(1H-indol-3-yl-methyl)-1'-methy-imidazolidine-2'4'-dione.

To a solution of 7-Phenoxy-3,4-dihydro-2H-quinoline-4-spiro-5'-3'-(1H-indol-3-ylmethyl)-1'-methyl-imidazolidine-2',4'-dione (1 eq.) in DCM (3–4 mL) will be treated with 4-formyl-piperidine-1-carboxylic acid tert butyl ester (1.2 eq.) and NaBH(OAc)$_3$ (2 eq). The reaction will be stirred at room temperature for 10–12 h and then worked up following the usual workup. The reaction crude will be purified by chromatography on silica gel using the suitable DCM/EtOAc mixture as eluent.

56E: Preparation of 7-Phenoxy-3'-4'-dihydro-2H-quinoline-1-(methylpiperidine-4yl)-4-spiro-5'-3'-(1H-indol-3-yl-methyl)-1'-methy-imidazolidine-2'4'-dione.

To a solution of 7-Phenoxy-3'-4'-dihydro-2H-quinoline-1-[(methylpiperidine-4-yl)-1-carboxylic acid tert-butyl ester]-4-spiro-5'-3'-(1H-indol-3-yl-methyl)-1'-methy-imidazolidine-2'4'-dione (1 eq.) in DCM (2–3 mL) will be treated with trifluoro acetic acid (TFA, 1 eq). The resulting mixture will be stirred at room temperature for 10–15 min, after that it will be quenched by addition of 2N NaOH aqueous solution to reach pH 7 and extracted with DCM (3×10 mL). The organic layer will be washed with water and brine and dried over Na$_2$SO$_4$. The reaction rude will be purified by chromatography on silica gel sing the suitable DCM/EtOAc mixture as eluent.

Example 57

Preparation of 7-(4-Tolyloxy)-3'-4'-dihydro-2H-quinoline-1-(methylpiperidine-4-yl)-4-spiro-5'-3'-methyl-1'-[2(-1H-indol-3-yl)-ethyl]-imidazolidine-2',4'-dione A compound of Formula I, where R$^1$ is tolyl, R$^2$ is methylpiperidin-4-yl, R$^3$ is methyl, and R$^4$ is 2(1H-indol-3-yl)ethyl can be prepared by following the synthetic procedures.

57A: Preparation of 7-Benzyloxy-3,4-dihydro-2H-quinoline-1-carboyxlic acid benzyl ester-4-spiro-5'-3'-methyl-imidazoline-2',4'-dione.

To a solution of Compound 5, where R$^1$ is benzyl, and R$^{2A}$ is benzyl in anhydrous DMF (8 mL) at room temperature will be added cesium bicarbonate (12 equivalents). The suspension will be stirred for 10–15 min and then MeI (1.2 equivalent) will be added. The reaction will be stirred for 8–12 hrs and after that it will be quenced with water and extracted with EtOAc (3×30 mL). The organic layer will be washed with water, brine, and dried over Na2SO4 and evaporated to dryness under vacuum. The resulting residue will be purified by chromatography on silica gel using a suitable mixture of DCM and EtOAC as eluent.

57B: Preparation of 7-Benzyloxy-3,4-dihydro-2H-quinoline-1-carboxylic acid benzyl ester-4-spiro-5'-3'-methyl-1'-[2(-1H-indol-3-yl)-ethyl-1-carboxylic acid tert-butyl ester]-imidazolidine-2'4'-dione.

To a solution of 7-Benzyloxy-3,4-dihydro-2H-quinoline-1-carboxylic acid benzyl ester-4-spiro-5'-3'-methyl-imidazolidine-2',4'-dione in anhydrous DMF (8 mL) at room temperature will be added $K_2CO_3$ (2 equivalents). The suspension will be stirred for 10–15 min. and then a solution of 3-(2-bromo-ethyl)-indole-1-carboxylic acid tert-butyl ester in DMF (2 mL) will be added. The reaction mixture will be stirred at room temperature for 15–18 h. The mixture will be then quenched with water and extracted with EtOAc (3×30 mL). The combined EtOAc layer will be washed with water, brine, dried over $Na_2SO_4$ and evaporated to dryness under vacuum. The resulting residue will be purified by chromatography on silica gel using the suitable mixture of DCM and EtOAc as eluent.

57C: 7-Hydroxy-3,4-dihydro-2H-quinoline-4-spiro-5'-3'-methyl-1'-[2(-1H-indol-3-yl)-ethyl)-1-carboxylic acid tert-butyl ester]-imidazolidine-2',4'-dione.

A solution of 7-Benzyloxy-3,4-dihydro-2H-quinoline-1-carboxylic acid benzyl ester-4-spiro-5'-1'-[2(-1H-indol-3-yl)-ethyl)-1-carboyxlic acid tert-butyl ester]-3'-methyl-imidazolidine-2'4'-dione will undergo hydrogenolysis as described in Example 34A.

57D: 7-Hydroxy-3,4-dihydro-2H-guinoline-1-[(methylpiperidine-4-yl)-1 carboxylic acid tert-butyl ester]-4-spiro-5'-3'-methyl-1'-[2(-1H-indol-3-yl)-ethyl)-1'-carboxylic acid tert-butyl ester]-imidazolidine-2'4'-dione.

A solution 7-Hydroxy-3,4-dihydro-2H-quinoline-4-spiro-5'-3'-methyl-1'-[2(-1H-indol-3-yl)-ethyl)-1-carboxylic acid tert-butyl ester]-imidazolidine-2,4'-dione in DCM (3 mL) will undergo the reductive-amination procedure taught in Example 49D using 4-formyl-piperidine-1-carboxylic acid tert butyl ester.

57E: 7-(4-Tolyloxy)-3,4-dihydro-2H-quinoline-1 [(methylpiperidine-4-yl)-1 carboxylic acid tert-butyl ester]-4-spiro-5'-3'-methyl-1'-[2(-1H-indol-3-yl)-ethyl)-1-carboxylic tert-butyl ester]-imidazolidine-2'4'-dione.

A solution of 7-Hydroxy-3,4-dihydro-2H-quinoline-1 [(methyl piperidine-4-yl)-1 carboxylic acid tert-butyl ester]-4-spiro-5'-3'-methyl-1 '-[2(-1H-indol-3-yl)-ethyl)-1-carboxylic acid tert-butyl ester]-imidazolidine-2'4'-dione in DCM will undergo the coupling conditions as taught for 7-(Tolyloxy)-3'-4'-dihydro-2H-quinoline-1'-(1H-indol-3-yl-methyl)-3'methyl-imidazolidine-2',4'-dione (see Example 38A).

57E: Preparation of 7-(4-Tolyloxy)-3,4-dihydro-2H-quinoline-1-[(methyl piperidine-4-yl)-4-spiro-5'-3'-methyl-1'-[2(-1H-indol-3-yl)-ethyl]-imidazolidine-2'4'-dione.

A solution of 7-(4-tolyloxy)-3,4-dihydro-2H-quinoline-1 [(methyl piperidine-4-yl)-1 carboxylic acid tert-butyl ester]-4-spiro-5'-3'-methyl-1'-[2(1H-indol-3-yl)ethyl]-1-carboxylic acid tert butyl ester]-imidazolidine-2',4'-dione in DCM will be de-protected by following the procedure taught for 7-phenoxy-3'-4'-dihydro-2H-quinoline-1-(methylpiperidine-4-yl)-4-spiro-5'-3'-methyl-1'-(1H-indol-3-yl-methyl)-imidazolidine-2'4'-dione.

Example 58

Determination of Biochemical and Radio Ligand Binding

This example teaches representative compounds of the present invention that have binding activity to receptors that are known to be associated with various therapeutic disorders.

Compounds A (Example 28), B (Example 26A), C (Example 49C), D (Example 41A), E (Example 37A), F (Example 50C), G (Example 51C), H (Example 41A), I (Example 52C), and J (Example 48A), as shown in Table 3, were assayed against selected somatostatin assays (sst1, sst2, sst3, sst4, and sst5) for biochemical binding using Somatostatin-14 as a reference according to the following protocols previous taught in the specification (see Table 4).

TABLE 3

| Comp | $R^1$ | $R^2$ | $R^3$ | $R^4$ |
|---|---|---|---|---|
| A | phenyl | 4-amino-1-yl-butan-1-one | (1H-indol-3-yl-methyl) | methyl |
| B | phenyl | 4-butylamino-1-yl | methyl | 1H-indol-3-ylmethyl |
| C | phenyl | 4-amino-1-yl-butan-1-one | methyl | 1H-indol-3-ylmethyl |
| D | tolyl | 4-butylamino-1-yl | methyl | 1H-indol-3-yl-methyl |
| E | phenyl | methyl piperidin-4-yl | methyl | 1H-indole-3-yl-methyl |
| F | hydrogen | 4-butyl amino-1-yl | [2-(1H-indol-3-yl)-ethyl] | methyl |
| G | 4-methoxy-phenyl | 4-amino butyl-1-yl- | [2-(1H-indol-3-yl)-ethyl] | methyl |
| H | tolyl | 4-butyl amino-1-yl | [2-(1H-indol-3-yl)-ethyl] | methyl |
| I | 3,4-dimethyl-phenyl | 4-butyl amino-1-yl- | [2-(1H-indol-3-yl)-ethyl] | methyl |
| J | benzo[1,3] dioxol | 4-butyl amino-1-yl | 2-(1H-indol-3-yl) ethyl | methyl |

TABLE 4

| Compound | Assay | Species | Conc ($\mu$M) | % inh | $IC_{50}$ ($\mu$M) | $EC_{50}/IC_{50}$ ($\mu$M) | $k_i$ ($\mu$M) | nH | % Ag | % Ant |
|---|---|---|---|---|---|---|---|---|---|---|
| A | $Sst_1$ (binding) | human | 10 | 54 | 6.39 | | 6.07 | 0.433 | | |
| | $Sst_2$ (functional) | ileum, gp | 3 | | | 2.9 | | | 58 | ND |
| | $Sst_3$ (binding) | human | 10 | 56 | 6.59 | | 5.85 | 0.564 | | |
| | $Sst_4$ (binding) | human | 10 | 50 | 6 | | 5.27 | 0.504 | | |
| | $Sst_5$ (functional) | Vas def gp | 30 | | | 19.4 | | | 61% | ND** |
| B | $Sst_1$ (binding) | human | 10 | 57 | 3.25 | | 3.09 | 0.62 | | |
| | $Sst_2$ (functional) | ileum, gp | 100 | | | 33.1 | | | 114 | ND |
| | $Sst_3$ (binding) | human | 10 | 60 | 5.84 | | 5.18 | 0.722 | | |
| | $Sst_4$ (binding) | human | 10 | 39 | | | | | | |
| C | $Sst_1$ (binding) | human | 10 | 24 | | | | | | |
| | $Sst_2$ (functional) | ileum, gp | 30 | | | | | | 44% | |
| | $Sst_3$ (binding) | human | | 25 | | | | | | |
| | $Sst_4$ (binding) | human | | 32 | | | | | | |

TABLE 4-continued

| Compound | Assay | Species | Conc (μM) | % inh | IC$_{50}$ (μM) | EC$_{50}$/ IC$_{50}$ (μM) | k$_i$ (μM) | nH | % Ag | % Ant |
|---|---|---|---|---|---|---|---|---|---|---|
| D | Sst$_1$ (binding) | human | 10 | 84 | 0.807 | | 0.767 | 0.654 | | |
| | Sst$_2$ (functional) | ileum, gp | 30 | | | 23.3 | | | 68 | ND |
| | Sst$_3$ (binding) | human | | 68 | 7.05 | | 6.26 | 2.34 | | |
| | Sst$_4$ (binding) | human | | 68 | 5.13 | | 4.51 | 1.15 | | |
| E | Sst$_1$ (binding) | human | 10 | 89 | 1.86 | | 1.77 | 1.16 | | |
| | Sst$_2$ (functional) | ileum, gp | | | | 10.5uM | | | 82 | ND |
| | Sst$_3$ (binding) | human | | 86 | 1.53 | | 1.36 | 1.3 | | |
| | Sst$_4$ (binding) | human | | 89 | 1.59 | | 1.4 | 1.37 | | |
| F | Sst$_1$ (binding) | human | 10 | 87 | 1.32 | | 1.25 | 0.992 | | |
| | Sst$_2$ (functional) | ileum, gp | 30 | | | 37 | | | 42% | ND |
| | Sst$_3$ (binding) | human | | | | | | | | |
| | Sst$_4$ (binding) | human | | | | | | | | |
| G | Sst$_1$ (binding) | human | 10 | 64 | 4.11 | | 3.9 | 0.67 | | |
| | Sst$_2$ (functional) | ileum, gp | 10 | | | NR | | | −2% | 0% |
| | Sst$_3$ (binding) | human | | 60 | 6.61 | | 5.87 | 0.985 | | |
| | Sst$_4$ (binding) | human | 10 | 68 | 3.87 | | 3.4 | 0.786 | | |
| H | Sst$_1$ (binding) | human | 10 | 66 | 1.24 | | 1.18 | 1.38 | | |
| | Sst$_2$ (functional) | ileum, gp | 10 | | | NR | | | −24% | 0 |
| | Sst$_3$ (binding) | human | | 57 | 7.58 | | 6.73 | 0.922 | | |
| | Sst$_4$ (binding) | human | | 68 | 0.649 | | 0.57 | 1 | | |
| I | Sst$_1$ (binding) | human | 10 | 66 | 3.38 | | 3.21 | 0.598 | | |
| | Sst$_2$ (functional) | ileum, gp | 30 | | | NR | | | 44% | 10% |
| | Sst$_3$ (binding) | human | 10 | 56 | 7.96 | | 7.06 | 0.977 | | |
| | Sst$_4$ (binding) | human | 10 | 71 | 2.62 | | 2.3 | 1.16 | | |
| J | Sst$_1$ (binding) | human | 10 | 69 | 0.699 | | 0.664 | 1.28 | | |
| | Sst$_2$ (functional) | ileum, gp | 30 | | | 22.9 | | | 55% | ND |
| | Sst$_3$ (binding) | human | | 72 | 3.71 | | 3.29 | 0.915 | | |
| | Sst$_4$ (binding) | human | 10 | 72 | 0.754 | | 0.663 | 1.25 | | |
| | Sst$_5$ (functional) | | 30 | | | | | | −11% | 1% |

Although the invention has been described with reference to the disclosed embodiments, it should be understood that various modifications can be made without departing from the spirit of the invention. Accordingly, the invention is limited only by the following claims.

What is claimed:

1. A compound of Formula I,

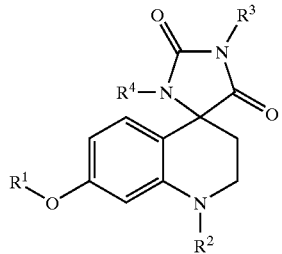

Formula I wherein,

R$^1$ is aryl, substituted-aryl, or aryl-(lower-alkyl)-;

R$^2$ is lower alkyl, amino substituted lower alkyl, -carboxy-(lower-alkyl), -carbamic acid-(lower-alkyl) or -carboxy-(lower-alkyl)-aryl; and R$^3$ and R$^4$ are independently, lower-alkyl, or lower alkyl substituted with indole;

or a pharmaceutically acceptable, ester, ether, or salt thereof.

2. The compound of claim 1, wherein R$^1$ is aryl.

3. The compound of claim 1, wherein R$^1$ is substituted-aryl.

4. The compound of claim 1, wherein R$^1$ is -(lower-alkyl)-aryl.

5. The compound of claim 1, wherein R$^3$ is lower-alkyl, or lower alkyl substituted with indole.

6. The compound of claim 1, wherein R$^4$ is lower-alkyl, or lower alkyl substituted with indole.

7. A compound of Formula II,

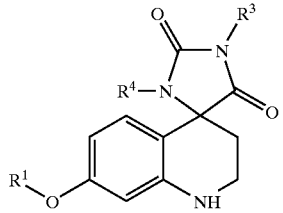

Formula II wherein,

R$^1$ is lower-alkyl, substituted lower-alkyl, aryl, substituted-aryl, aryl-(lower-alkyl)-, (substituted-aryl)-(lower-alkyl)-, heteroaryl, heteroaryl-(lower-alkyl)-, substituted-heteroaryl, (substituted-heteroaryl)-(lower-alkyl)-, heterocyclic, heterocyclic-(lower-alkyl)-, substituted heterocyclic, or (substituted-heterocyclic)-(lower-alkyl)-; and R$^3$ and R$^4$ are independently, lower-alkyl or lower alkyl substituted with indole.

8. A compound of Formula III,

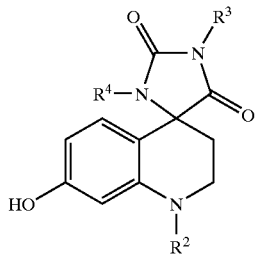

Formula III wherein, $R^2$ is lower alkyl, amino substituted lower alkyl, lower-alkyl carbonyl, -carboxy-(lower-alkyl), or -carboxy-(lower-alkyl)-aryl; and $R^3$ and $R^4$ are independently, lower-alkyl or lower alkyl substituted with indole.

9. A compound of Formula IV,

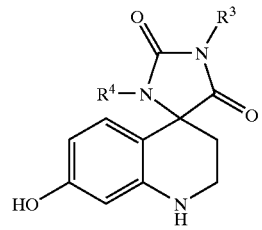

Formula IV wherein, $R^3$ and $R^4$ are independently, lower-alkyl or lower alkyl substituted with indole.

* * * * *